(12) United States Patent
Dantus et al.

(10) Patent No.: US 11,274,982 B2
(45) Date of Patent: *Mar. 15, 2022

(54) MATERIALS AND APPARATUS WITH MULTIPLE IMPACT LEVEL AND TORQUE DETECTION

(71) Applicant: BOARD OF TRUSTEES OF MICHIGAN STATE UNIVERSITY, East Lansing, MI (US)

(72) Inventors: Marcos Dantus, Okemos, MI (US); Gary J. Blanchard, Okemos, MI (US); D. J. Osborn, III, Sa (AU); Elan Dantus, Okemos, MI (US); Sheryl Blanchard, Olemos, MI (US); Evan Blanchard, Okemos, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 64 days.

This patent is subject to a terminal disclaimer.

(21) Appl. No.: 16/546,705

(22) Filed: Aug. 21, 2019

(65) Prior Publication Data

US 2020/0041367 A1 Feb. 6, 2020

Related U.S. Application Data

(63) Continuation of application No. 15/164,996, filed on May 26, 2016, now Pat. No. 10,444,100.

(Continued)

(51) Int. Cl.
*G01L 5/00* (2006.01)
*A61B 5/369* (2021.01)

(52) U.S. Cl.
CPC ............ *G01L 5/0052* (2013.01); *A61B 5/369* (2021.01)

(58) Field of Classification Search
CPC ................. G01L 5/0052; A61B 5/0476; A61B 5/6802–5/6804
See application file for complete search history.

(56) References Cited

U.S. PATENT DOCUMENTS

| 2,730,457 A | 1/1956 | Green et al. |
| 4,888,334 A | 12/1989 | Ohga et al. |

(Continued)

FOREIGN PATENT DOCUMENTS

| WO | WO-2014/008031 A1 | 1/2014 |
| WO | WO-2016/014355 A1 | 1/2016 |

OTHER PUBLICATIONS

Kamata et al., "Synthesis and Characterization of Monodispersed Core—Shell Spherical Colloids with Movable Cores," *J. Am. Chem. Soc.*, 125:2384-85 (2003).

(Continued)

*Primary Examiner* — Erika J Villaluna
(74) *Attorney, Agent, or Firm* — Marshall, Gerstein & Borun LLP

(57) ABSTRACT

The disclosure relates to materials and articles that provide an irreversible history of compression forces and torques experienced by the materials and articles. The disclosure relates more particularly to an multiple impact level detection assembly as well as related articles and methods. The multiple impact level detection assembly provides distinct impact patterns depending on the impact force and direction (for torqueing motions) received by the detection assembly. The detection assembly can be incorporated into a variety of articles and used in a variety of settings, for example to monitor personal safety in a protective garment such as a helmet. The detection assembly incorporates an impact detection medium (e.g., a plurality of microcapsules with an indicator therein), which can serve as an irreversible means (Continued)

for detecting impact on the assembly via a relief substrate incorporated into the assembly.

38 Claims, 9 Drawing Sheets

Related U.S. Application Data

(60) Provisional application No. 62/234,107, filed on Sep. 29, 2015.

(56) References Cited

U.S. PATENT DOCUMENTS

| | | |
|---|---|---|
| 4,903,991 A | 2/1990 | Wright |
| 5,142,309 A | 8/1992 | Lee |
| 8,387,552 B2 | 3/2013 | Branch |
| 8,556,831 B1 | 10/2013 | Faber et al. |
| 2006/0038694 A1 | 2/2006 | Naunheim et al. |
| 2006/0063125 A1 | 3/2006 | Hamilton et al. |
| 2012/0009391 A1 | 1/2012 | Dry |
| 2013/0118255 A1 | 5/2013 | Callsen et al. |
| 2014/0290561 A1 | 10/2014 | Noguchi |

OTHER PUBLICATIONS

Kijewska et al., "Photopolymerized Polypyrrole Microvessels," *Chem. Eur. J.*, 18:310-20 (2012).

Tiarks et al., "Preparation of Polymeric Nanocapsules by Miniemulsion Polymerization," *Langmuir*, 17:908-18 (2001).

Wang et al., "Template Synthesis of Nanostructured Materials via Layer-by-Layer Assembly," *Chem. Mater.*, 20:848-58 (2008).

International Search Report and Written Opinion for International application No. PCT/US2015/040883, dated Oct. 9, 2015.

MATERIALS AND APPARATUS WITH MULTIPLE IMPACT LEVEL AND TORQUE DETECTION

CROSS REFERENCE TO RELATED APPLICATION

This application is a continuation of U.S. patent application Ser. No. 15/164,996 (filed May 26, 2016), which claims priority to U.S. Provisional Application No. 62/234,107 (filed on Sep. 29, 2015), which are incorporated herein by reference in their entireties.

STATEMENT OF GOVERNMENT INTEREST

None.

BACKGROUND OF THE DISCLOSURE

Field of the Disclosure

The disclosure relates to materials and articles that provide an irreversible history of compression forces and torques experienced by the materials and articles. The disclosure relates more particularly to a multiple impact level detection assembly as well as related articles and methods. The multiple impact level detection assembly provides distinct impact patterns depending on the impact force and direction (for torqueing motions) received by the detection assembly. The detection assembly can be incorporated into a variety of articles and used in a variety of settings, for example to monitor personal safety in a protective garment such as a helmet.

SUMMARY

There is a need to track the force and impact exerted by athletes during their regular practices and in their games. In many cases, the accumulated force/impact can be helpful to track effort and performance, and other times it can be helpful to detect injury. In particular, in American football and other contact sports, it is important to track head impact. The development of a simple, inexpensive, and preferably disposable media to track force/impact addresses this need. Coaches, trainers, and medical personnel in various sports including football will be able to track the performance of every one of their players and keep a record of the force/impact experienced by, for example, their feet, knees, shoulders, and/or head.

Current approaches in impact measurement for football helmets include in the helmets one or more accelerometers and their associated electronics and means to communicate to a computer or recording device. The inclusion of electronics greatly increases the complexity and cost of the solution. In addition, electronic approaches are more prone to malfunction in general or as a result of impact during normal use. Electronic approaches are also subject to electronic tampering.

In contrast, the disclosed multiple impact level detection assembly does not rely on electronic components, it is inexpensive, and it can be disposable (e.g., entirely disposable, or partially disposable and partially reusable), making it accessible to a much greater audience of potential users who can benefit from the additional safety information provided by the detection assembly. The detection assembly provides a simple recording medium that can be read without the need for electronic devices. While accelerometers and gyroscopes measure linear acceleration and angular acceleration, respectively, the disclosed detection assembly measures force/impact. This is more useful because it is insensitive to large-acceleration movements and a correspondingly large force (e.g., if an athlete throws the helmet on the floor, the detection assembly will not record a significant force due to the lack of the head mass impacting against the helmet.).

This disclosed multiple impact level detection assembly also provides a permanent record of a force/impact experienced by the athlete that can be used by coaches, trainers, and medical personnel to assess severity of impact and/or effort exerted to make appropriate decisions (e.g., allow a player to continue to play in a game, remove a player from a game, provide medical attention to a player).

This disclosed multiple impact level detection assembly also provides a simple path towards producing calibrated impact media that can address a wide range of forces/impacts depending on the application. For example, the detection assembly can be adjusted by sport, application, gender, size, weight, type and model of the equipment to which the detection assembly is attached.

In an embodiment, the disclosed multiple impact level detection assembly utilizes existing media on paper or polymeric matrices that contain microencapsulated ink or dyes. Such type of media includes microencapsulated stock (MES) and is described in U.S. Pat. No. 2,730,457 (as carbonless copy paper) and U.S. Pat. No. 5,142,309 (as a recording medium for golf club impact location). The MES medium has only two states: When it is fresh or otherwise non-impacted it is white or clear; when a sufficient force impacts it, it develops a visible color. However there is no graduation or ability gauge the relative force impact of the basic MES material. Pressure activates the MES; the disclosed multiple impact level detection assembly uses the relationship that pressure is proportional to force divided by area. The detection assembly pairs the MES with a patterned relief substrate such that a patterned relief surface, when contacted with the MES, can be used to measure the force of an impact based on the pattern activated by and permanently marked on the MES in a calibrated manner (e.g., because different minimum threshold levels of impact are required to activate different distinct patterns). For example, when an athlete wearing a helmet with the detection assembly with the MES receives an impact, the MES will reveal a pattern that is proportional to the impact force received by the head. This is based on two relationship: Pressure equals force divided by area and force equals mass times acceleration. The pattern on the MES will record the pressure exerted by the head after attenuation by the padding. The pattern records the pressure and, given that each pattern has a different calibrated contact area, it reveals the force. Once the force is known, knowledge of the mass of the head yields a good estimate for the acceleration experienced by the head.

The detection assembly includes a substrate containing a relief pattern that presents different surface areas to the MES such that the recorded pattern can be easily read and converted to the calibrated force. It is this pattern that converts an otherwise digital substrate (activated or not activated) into an analog recorder that is proportional to the force acted on it.

In one aspect, the disclosure relates to a multiple impact level detection assembly comprising: (a) a first substrate having a top surface, an opposing bottom surface, and an interior substrate volume between the top surface and the bottom surface; (b) a relief substrate having a top surface, an opposing bottom surface, and an interior substrate volume between the top surface and the bottom surface, wherein: (i) the relief substrate bottom surface opposes the first substrate top surface, and (ii) the relief substrate bottom surface comprises at least two contact regions having different separation distances from the first substrate top surface; and (c) an impact detection medium positioned at one or more of the first substrate top surface, the first substrate interior volume, the first substrate bottom surface, and the relief substrate contact regions, wherein the impact detection medium has a characteristic impact threshold for generating a detectable property (e.g., an optical property) associated with the impact detection medium. In a refinement, the impact detection medium is positioned at the first substrate top surface. In a refinement, the impact detection medium is positioned at the first substrate interior volume. In a refinement, the impact detection medium is positioned at the first substrate bottom surface. In a refinement, the impact detection medium is positioned at the relief substrate contact regions. In another refinement, the multiple impact level detection assembly further comprising a means for attachment on one or both of an outer surface of the first substrate and an outer surface of the relief substrate. In another refinement, the detectable property is an optical property.

Various refinements of the multiple impact level detection assembly are possible. For example, the contact regions can have a general shape selected from the group consisting of a flat surface parallel to the opposing first substrate top surface, a curved or flat surface sloped relative to the opposing first substrate top surface, an edge, a point, and combinations thereof. In another refinement, the assembly is configured to be worn on a person's head, for example further comprising elastic headwear configured to maintain the assembly in a substantially fixed position on the person's head when worn. In another refinement, the relief substrate comprises a plurality of relief elements, each relief element comprising at least two contact regions having different separation distances from the first substrate top surface, for example wherein the relief elements have a uniform size and shape on the relief substrate or wherein the relief elements have a variable size and shape on the relief substrate. In another refinement, the relief substrate comprises a plurality of relief elements, each relief element comprising at least two contact regions having different separation distances from the first substrate top surface, the assembly is configured to be worn on a person's head, and the relief elements are positioned in locations corresponding to electroencephalography (EEG) locations on the wearer's head. In another refinement, the separation distance for at least one contact surface is zero. In another refinement, the multiple impact level detection assembly further comprises: (d) a sleeve at least partially enclosing the first substrate, the relief substrate, and the impact detection medium. In another refinement, the impact detection medium is positioned at one or more of the first substrate top surface, the first substrate interior volume, and the first substrate bottom surface; and the first substrate is adapted to be removable and replaceable. In another refinement, at least one of the first substrate and the relief substrate are optically translucent or transparent. In another refinement, the multiple impact level detection assembly further comprises a means for attachment on one or both of an outer surface of the first substrate and an outer surface of the relief substrate.

In a class of embodiments, the impact detection medium comprises a plurality of microcapsules each comprising an outer shell defining an interior volume and an indicator contained in the interior volume, wherein each microcapsule has a characteristic impact threshold prior to rupture of the microcapsule and release of the indicator from the interior volume to generate an irreversible change in a detectable property associated with the indicator. In a refinement, the characteristic impact threshold of the microcapsule has been selected by controlling one or more of reaction solvent, polymerization initiator, monomer, ionic strength, reaction medium pH, reaction temperature, reaction time, and UV light exposure during a polymerization process forming the microcapsule. In another refinement, the detectable property is selected from the group consisting of an optical property, an olfactory property, a chemical property, an electrical property, an electromagnetic property, and combinations thereof. In another refinement, the plurality of microcapsules comprises: (A) a plurality of first microcapsules containing a first indicator therein and having a first characteristic impact threshold; and (B) a plurality of second microcapsules containing a second indicator therein and having a second characteristic impact threshold; wherein: the detectable property of the first indicator is different from the detectable property of the second indicator, and the first characteristic impact threshold is different from the second characteristic impact threshold.

In another aspect, the disclosure relates to an article of clothing comprising the multiple impact level detection assembly according to any of the variously disclosed embodiments spatially positioned in or on the article of clothing to detect impact experienced by a wearer of the article of clothing. For example, the article be an article of clothing such as a headband or cap which does not provide substantial protection to the body part (e.g., head), but which measures the impact sustained by the body part. The article can be useful in contact sports which do not utilize protective headgear (for example) such as soccer (global football) and rugby, but for which it can be desirable to know when and whether a user's head sustains a potentially damaging impact.

In another aspect, the disclosure relates to a protective garment (e.g., a helmet or a wearable guard for other than a head body part) comprising the multiple impact level detection assembly according to any of the variously disclosed embodiments spatially positioned in or on the protective garment to detect impact experienced by a wearer of the protective garment. In a particular embodiment, the protective garment comprises: (a) a protective shell having (i) an outer surface and (ii) an opposing inner surface; (b) protective padding having (i) an outer surface, (ii) an opposing inner surface, and (iii) an interior padding volume between the outer surface and the inner surface, wherein the protective padding is mounted at the outer surface thereof to the protective shell at the inner surface thereof; and (c) the multiple impact level detection assembly according to any of the variously disclosed embodiments positioned at one or more of: (i) an interface between the protective shell inner surface and the protective padding outer surface, (ii) the interior padding volume, (iii) the protective padding inner surface, and (iv) the protective shell outer surface. In a refinement, the protective garment is a helmet. In another refinement, the protective garment is a wearable guard for other than a head body part. In another refinement, the multiple impact level detection assembly is positioned at the interface between the protective shell inner surface and the protective padding outer surface. In another refinement, the multiple impact level detection assembly is positioned at the protective padding inner surface (e.g., a preferred embodiment in which the detection assembly is located at the portion of the protective garment that is in nearest proximity to the user's body during use of the protective garment, thus given a representative indication of the force experienced by the user upon an impact).

In a particular refinement, the multiple impact level detection assembly is positioned such that the impact detection medium can be interrogated by visual inspection when the protective garment is not being worn and without disassembling the protective garment. For example, the protective garment (e.g., helmet) can be removed from the user, and any impacts recorded on the impact detection medium can be viewed without removing any components from the detection assembly or the protective garment more generally. For instance, when the detection assembly is oriented such as illustrated in FIG. 13 (described below) in a protective garment such as a helmet, the impact detection substrate is positioned at an externally viewable location (e.g., when the sleeve is transparent or not present). The first substrate with the impact detection medium can be removed and replaced if desired without disassembling with protective garment. Similarly, the appropriate medical action can be taken without disassembling with protective garment if visual inspection of the impact detection medium suggests that a dangerous impact and/or torque has been sustained.

In another aspect, the disclosure relates to a method for equipping a protective garment with a means for detecting impact, the method comprising: (a) providing a protective garment comprising: (i) a protective shell having (A) an outer surface and (B) an opposing inner surface, and (ii) protective padding having (A) an outer surface, (B) an opposing inner surface, and (C) an interior padding volume between the outer surface and the inner surface; (b) attaching the multiple impact level detection assembly according to any of the variously disclosed embodiments to one or more of: (i) the protective padding outer surface, and (ii) the protective padding inner surface; and (c) mounting the protective padding at the outer surface thereof to the protective shell at the inner surface thereof.

In another aspect, the disclosure relates to a kit comprising: (a) a multiple impact level detection assembly according to any of the variously disclosed embodiments; and (b) protective padding sized and shaped for insertion into a protective shell of a protective garment, the protective padding having (i) an outer surface, (ii) an opposing inner surface, and (iii) an interior padding volume between the outer surface and the inner surface.

In another aspect, the disclosure relates to a method for detecting impact on a protective garment worn by a user, the method comprising: (a) wearing the protective garment according to any of the variously disclosed embodiments (e.g., a user wearing the protective garment during participation in sport or other contact activity); (b) impacting the protective garment (e.g., resulting from contacting or colliding with another sport participant or the environment); and (c) interrogating the impact detection medium of the protective garment after (b) to determine whether the protective garment has sustained an impact force exceeding a characteristic impact threshold at one or more of the contact surfaces of the relief substrate (e.g., evaluation, observation, measurement, etc. of one or more of the particular detectable property(ies) of the detection assembly and corresponding impact detection medium, such as by human observation (e.g., visual), machine-assisted detection; step of interrogating can be during or after game). The detected impact can be in the form of a compressive impact or a torqueing impact involving significant angular acceleration (e.g., such as that measured by a gyroscope). In a refinement, the contact regions have a general shape selected from the group consisting of an edge, a point, and combinations thereof; and interrogating the impact detection medium comprises determining whether the protective garment has sustained a torqueing impact and the direction of same.

In another refinement, the method further comprises (d) if the protective garment has sustained an impact force exceeding the characteristic impact threshold, determining whether the impact force is dangerous to the user (e.g., whether the impact is sufficiently intense to elicit medical evaluation of the user). For example, a low-level detection could indicate the that wearer has sustained a low-level, safe impact; but a high-level detection could indicate that the wearer has sustained a potentially dangerous impact, and follow-up actions can include performing one or more of (i) removing the user from an ongoing impact environment (e.g., an ongoing sporting contest where the user is removed from further game participation), (ii) investigating the user for an impact-related injury, and (iii) treating the user for an impact-related injury (e.g., a concussion for helmet protective garments; a bone fracture, internal bleeding or other physical damage for the corresponding protective garment body parts more generally).

In another aspect, the disclosure relates to a kit comprising: (a) a multiple impact level detection assembly according to any of the disclosed embodiments; and (b) an elastic wearable garment adapted to maintain the detection assembly in position relative to a user's body. For example, the detection assembly in the kit cab be sized and shaped for a specific sport and helmet design. The wearable garment can be of a particular color combination to match that of a particular team or personal preference. In a refinement, the garment can be a headband or a cap (e.g., skull cap). In another refinement, the kit can comprise a plurality of multiple impact level detection assemblies according to any of the disclosed embodiments, for example where the multiple impact level detection assemblies are adapted to replace an existing multiple impact level detection assembly mounted in the garment (e.g., where the existing detection assembly has registered an impact or it otherwise damaged and in need of replacement before the garment is re-used in a high-impact activity).

While the disclosed articles, methods and compositions are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

BRIEF DESCRIPTION OF THE DRAWINGS

For a more complete understanding of the disclosure, reference should be made to the following detailed description and accompanying drawings wherein.

DETAILED DESCRIPTION

Figure 1:
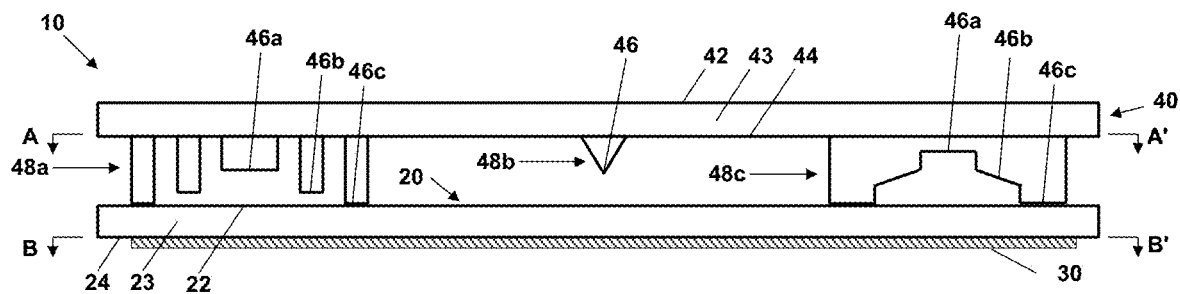
FIG. 1 is a side cross sectional view of a multiple impact level detection assembly according to the disclosure and including various relief substrates and an external surface impact detection medium.

The disclosure relates to materials and articles that provide an irreversible history of compression forces and torques experienced by the materials and articles. The disclosure relates more particularly to a multiple impact level detection assembly as well as related articles and methods. The multiple impact level detection assembly provides distinct impact patterns depending on the impact force and direction (for torqueing motions) received by the detection assembly, whether directly or indirectly through a protective garment into which the detection assembly is incorporated. The detection assembly can be incorporated into a variety of articles and used in a variety of settings, for example to monitor personal safety in a protective garment such as a helmet. The detection assembly incorporates an impact detection medium (e.g., a plurality of microcapsules with an indicator therein), which can serve as an irreversible means for detecting impact on the assembly via a relief substrate incorporated into the assembly. Impact detection is irreversible in the sense that an impact (e.g., impact force, shearing or torqueing force) experienced by the impact detection medium of the assembly above a characteristic threshold level induces an irreversible detectable change associated with the impact detection medium (e.g., force- and/or torque-induced rupture of microcapsules which can release a detectable color indicator, among other options, as described below). The impact detection medium imparts impact memory to the detection assembly, because the impact-induced change in the impact detection medium provides a permanent, detectable indication of the impact event (e.g., the occurrence of the event, the location of the event, the relative intensity of the event, and/or the direction of a torqueing or shearing event), even after the impact event is completed. The irreversible detectable change further provides a tamper-proof and non-electronic means for detecting a shock or impact.

FIGS. 1-13 illustrate several embodiments of a multiple impact level detection assembly 10 according to the disclosure.

With specific reference to FIGS. 1-5, the multiple impact level detection assembly 10 includes a first substrate 20, a relief substrate 40, and an impact detection medium 30. The first substrate 20 has a top surface 22, an opposing bottom surface 24, and an interior substrate volume 23 between the top surface 22 and the bottom surface 24. Similarly, the relief substrate 40 has a top surface 42, an opposing bottom surface 44, and an interior substrate volume 43 between the top surface 42 and the bottom surface 44. The first substrate 20 and the relief substrate 40 are illustrated as being flat or planar, but they more generally can have any desired shape that is suitable for the intended use of the detection assembly 10. For instance, the detection assembly 10 and corresponding substrates 20, 40 can have a curved shape, flat shape, or a combination of curved and flat sections to correspond to the contour of a personal protective garment (e.g., helmet or otherwise) and/or a user's body where the detection assembly 10 will be used to detect impact. As illustrated, the substrates 20, 40 can have an opposing face-to-face arrangement in which the relief substrate 40 bottom surface 44 opposes the first substrate 20 top surface 22.

The relief substrate 40 further includes two or more contact regions 46 extending from the body of the substrate 40 (e.g., represented by the interior substrate volume 43).

Figure 5:
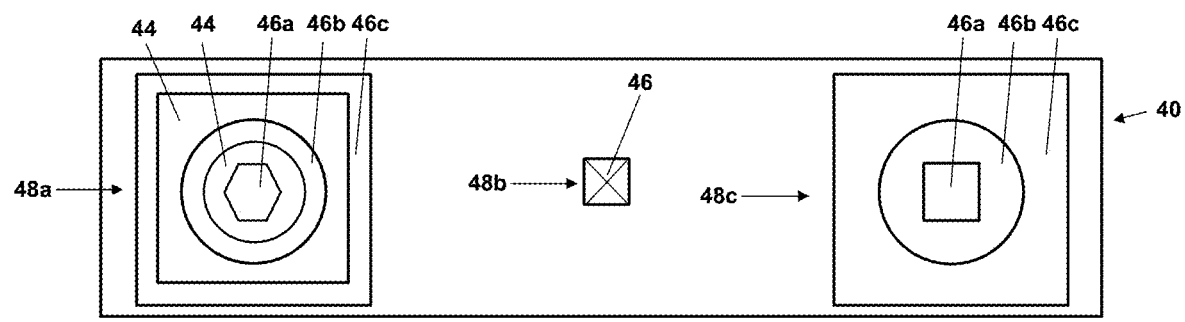
FIG. 5 is a bottom plan view A-A' of the multiple impact level detection assembly of FIG. 1 illustrating the various relief substrates.

For instance, the contact regions 46 can be extensions from the relief substrate 40 bottom surface 44, which extend towards the first substrate 20 (e.g., the top surface 22 thereof as illustrated). As illustrated, the contact regions 46 can be components of one or more relief elements 48 extending from the body of the substrate 40. The contact region 46 is a portion of the relief substrate 40 (e.g., bottom surface 40 thereof) that is capable of contacting the first substrate 20 top surface 22 under a compressive load on the relief substrate 40 and/or one or more of the relief elements 48. FIGS. 1 and 5 provide three illustrative embodiments for the relief elements 48: (i) a relief element 48a including three different contact regions 46a (an interior solid hexagonal shape), 46b (a middle circular ring shape), and 46c (an exterior square ring shape) as three different components with different heights, (ii) a relief element 48b having a pyramidal shape and including a single contact surface 46 (a point as the pyramid apex) with a single height for its apex, and (iii) a relief element 48c including three different contact regions 46a (an interior solid small square shape), 46b (a middle circular shape with the small square interior cut-out), and 46c (an exterior solid large square with the circular shape cut-out) from a single component but with different heights.

Figure 2:
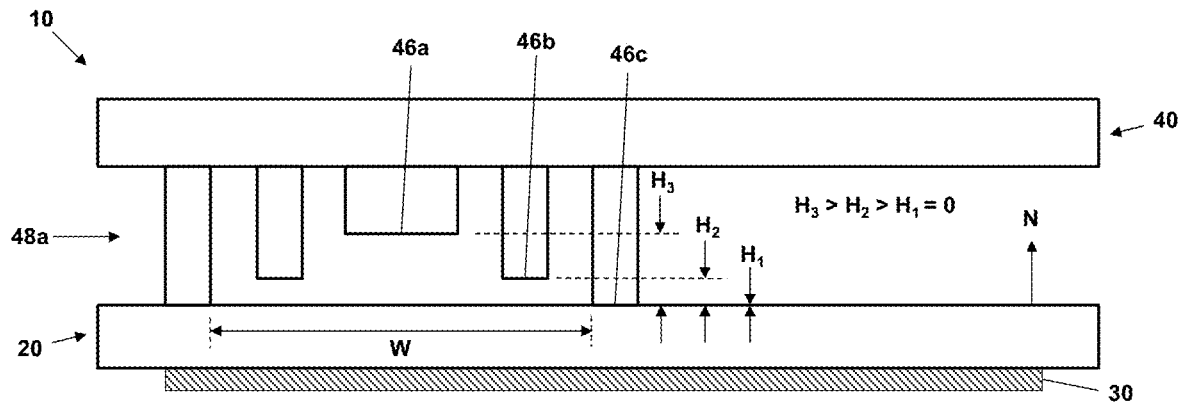
FIG. 2 is an expanded side cross sectional view of the multiple impact level detection assembly of FIG. 1 illustrating length scales and directions associated with the assembly.

The relief substrate 40 (and/or relief element 48) can have any desired shape, for example having two or more contact points or surfaces 46 that are defined by their position, surface area, rigidity, shape, texture, aspect ratio, separation distance and distance between contact surfaces 46. The shape of a relief element 48 and its contact points or surfaces 46 can be characterized by its three-dimensional shape and/or by its two-dimensional shape projected onto the relief substrate 40 (e.g., the bottom surface 44 thereof). The inclusion of two or more contact points or surfaces 46 can be used to detect multiple different levels of impact (e.g., compressive force) sustained between the first substrate 20 and relief substrate 40. For example, for a given relief substrate 40 (and/or relief element 48), preferably at least two contact regions 46 have different separation distances H from the first substrate 20 top surface 22 (e.g., at least 2, 3, 4, 5, 6, or 8 different separation distances and/or up to 3, 4, 6, 10, or 15 different separation distances corresponding to different impact levels). The separation distance H for a given contact region 46 is the distance between the first substrate 20 top surface 22 and the contact region 46 in the absence of a compressive force (e.g., absence of an applied or external force, but possibly including nominal compressive forces from the weight of a protective gear incorporating the detection assembly 10 or means for holding the first substrate 20 and the relief substrate 40 in contact with each other, such as a sleeve 50 described below). As illustrated in FIG. 2, the separation distance H can be measured in the direction of the local surface normal vector N of the first substrate 20 top surface 22 in the region generally opposing the contact region 46. The separation distance H for a given contact region 46 can be zero or greater than zero. Specifically, a contact region 46 can be in contact with (zero separation distance H) or separated from (greater than zero separation distance H) the first substrate 20 top surface 22 in the natural, non-compressed state of the detection assembly 10. Even with zero separation distance H, however, the characteristic impact threshold of an impact detection medium 30 and/or the compliant nature of the first substrate 20 and/or relief substrate 40 materials can result a minimum required compressive force to generate an impact signal or pattern 32 on the medium 30 (described below). In some embodiments, the separation distance H for at least one contact surface 46 is zero. In another embodiment incorporating some spacers (not shown) between the first substrate 20 and the relief substrate 40, there can be separation distances H that are all greater than zero for the contact surfaces 46. FIG. 2 illustrates three representative separation distances H for the relief element 48a: (i) contact surface 46a has the largest separation distance $H_3$, (ii) contact surface 46b has an intermediate separation distance $H_2$, and (iii) contact surface 46c has the lowest, zero separation distance $H_1$, such that $H_3 > H_2 > H_1 = 0$. As described below, the different separation distances H result in different impact levels being required to generate an impact pattern 32 (e.g., generally being proportional to H but having a threshold impact before any pattern 32 is generated). FIG. 2 further illustrates a characteristic lateral length scale or width dimension W of the relief element 48a.

In some embodiments, the relief substrate 40 (and/or relief element 48) can have a desired shape with only one contact point or surface 46 defined by its position, surface area, rigidity, shape, texture, aspect ratio, separation distance, for example when it is desired to measure the direction of an impact that creates a twisting, shearing, or torqueing motion between the first substrate 20 and relief substrate 40. FIGS. 1 and 5 illustrate such an embodiment with relief element 48b having a generally pyramidal shape and single contact point 46 at its apex.

The first substrate 20 and the relief substrate 40 are not particularly limited and may be formed from the same or different materials, for example from any desired compliant or non-compliant (e.g., rigid, incompressible, or resilient) material. The substrates 20, 40 can be thin, rigid or flexible materials such as polymer or plastic materials (e.g., sheet or film), cellulosic materials (e.g., paper or cardstock), metallic materials (e.g., steel or otherwise). Portions of the relief substrate 40 forming the contact surfaces 46 (e.g., the relief elements 48) are suitably a rigid or otherwise non-compliant material, which can assist the contact surfaces 46 in transferring and applying the necessary force to induce the change in the detectable property of the detection medium 30. For example, small metallic relief elements 48 on a flexible paper or cardstock substrate 40 can be used to deform a similarly flexible paper or cardstock substrate 20 and induce the change in the detectable property of the medium 30 thereon. The substrates 20, 40 (e.g., including the relief elements 48) can be formed by any suitable method such as molding, machining, three-dimensional printing, etc. The medium 30 and/or the relief elements 48 can be integrally formed with or separate structures attached to their respective substrates 20, 40. The substrates 20, 40 can be opaque, optically translucent, or transparent. In some embodiments, at least one of the first substrate 20 and the relief (or second) substrate 40 is optically translucent or transparent (e.g., in which case a visible impact pattern can be viewed therethrough).

Figure 3:
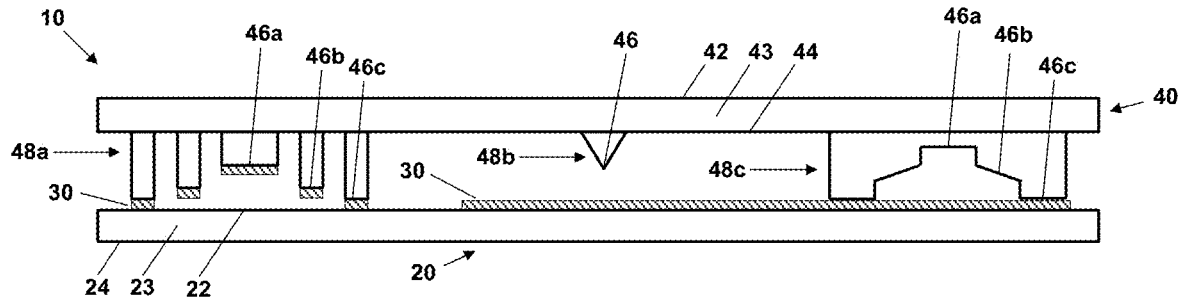
FIG. 3 is a side cross sectional view of a multiple impact level detection assembly according to the disclosure and including various relief substrates and an internal surface impact detection medium.
Figure 4:
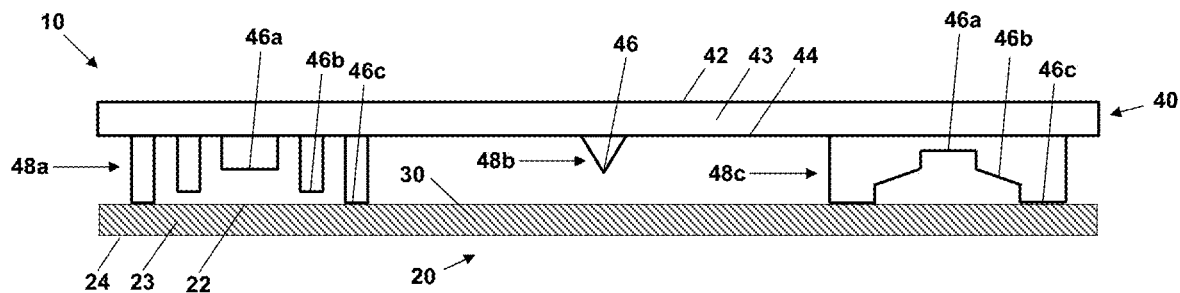
FIG. 4 is a side cross sectional view of a multiple impact level detection assembly according to the disclosure and including various relief substrates and an internal substrate impact detection medium.

The detection assembly 10 further includes an impact detection medium 30 located in, on, or as a component of the first substrate 20 and/or the relief substrate 40. The impact detection medium 30 has a characteristic impact threshold for generating a detectable property associated with the impact detection medium 30. The detectable property can be an optical property (e.g., suitably providing a visible marker or pattern identifiable to the naked human eye), an olfactory property, a chemical property, an electrical property, an electromagnetic property, and combinations thereof. As described below, the impact detection medium 30 can be a plurality of indicator-filled microcapsules, for example as described below and/or U.S. Pat. No. 2,730,457 (incorporated herein by reference in its entirety). In other embodiments, the impact detection medium 30 can be a deformable paper or polymeric/plastic substrate that can be permanently deformed and embossed with a visible and/or tactile pattern 32 corresponding to the contact surfaces 46/relief elements 48, where the compression force determines the extent with which the fine features of the pattern 32 marked. In some embodiments, the impact detection medium 30 can be a combination of the deformable substrate and the indicator-filled microcapsules (e.g., carbonless copy paper or otherwise). In yet other embodiments, impact detection medium 30 can be a pressure-sensitive film providing a visible indication of the distribution and magnitude of pressure impact received by the film (e.g., Fujifilm PRESCALE tactile pressure indicating sensor film). The impact detection medium 30 can be a layer on an external surface of the first substrate 20 and/or the relief substrate 40. Alternatively or additionally the impact detection medium 30 can be distributed throughout the first substrate 20 interior volume 23, such as in a composite-like structure where the first substrate 20 body forms a matrix for the distributed impact detection medium 30 therethrough (e.g., as distributed microcapsules). For example, as variously illustrated in FIGS. 1-4, the impact detection medium 30 can be positioned at the first substrate 20 bottom surface 24 (FIGS. 1 and 2), the first substrate 20 top surface 22 (FIG. 3, middle and right portions), the relief substrate 40 contact regions 46 (FIG. 3, left portion), and/or the first substrate 20 interior volume 23 (FIG. 4). The impact detection medium 30 can be on multiple surfaces (e.g., first substrate 20, relief substrate 40, and/or portions thereof), for example to make redundant measurements as a confirmation, or when different reactive components of a particular impact detection medium 30 are coated on different opposing surfaces which contact or otherwise generate a detectable signal upon compression.

The contact regions 46 can have any desired shape to make a recognizable impact pattern at a desired impact level. As illustrated in FIGS. 1 and 5, suitable shapes for contact regions 46 can include a flat surface parallel to the opposing first substrate 20 top surface 22 (e.g., as shown by surfaces 46a, 46b, and 46c of relief element 48a and by surfaces 46a and 46c of relief element 48c), a curved or a flat surface sloped (i.e., non-parallel) relative to the opposing first substrate 20 top surface 22 (e.g., as shown by surface 46b of relief element 48c), a point (e.g., as shown by apex 46 of relief element 48b), an edge (e.g., resulting from a relief element with a triangular cross-section protrusion; not shown), and combinations thereof (e.g., when a relief element includes multiple region 46 shapes). A parallel flat surface is intended to generally yield a binary yes/no result as a detectable impact pattern when an impact has exceeded a particular threshold level, although the intensity of the detectable property and the coverage of detectable property of the impact pattern across the surface of the impact medium 30 can depend to some extent on the level of impact (e.g., a relatively darker or otherwise stronger impact pattern resulting from an impact substantially exceeding the threshold detection level for a given contact region 46). A curved or flat sloped (or non-parallel) surface is intended to generally yield a graduated result when an impact has exceeded a particular threshold level, where the fractional coverage of the impact medium 30 of the detectable property relative to the contact region 46 corresponding more directly to the level of impact. Edges 46 and points 46 can be distal protrusions of pyramidal, conical, or other protrusions extending from the relief substrate 40, and they are able to trace out detectable paths for torqueing motion and impact.

The shape of the contact region 46 as a two-dimensional projection onto the relief substrate 40 bottom surface 44 corresponds to the two-dimensional shape of the corresponding impact pattern 32 resulting from an impact above the particular threshold level for the contact region. Suitably, the contact regions 46 and corresponding impact patterns 32 have distinct and easily differentiable sizes and/or shapes to facilitate rapid interrogation of the detection assembly 10 after an impact. Representative shapes include circles, ovals, squares, rectangles, triangles, pentagons, hexagons, other polygons, stars, lines, dots, letters, numbers, combinations of letters and/or numbers (e.g., forming codes and/or words such as "warning" or "danger") etc. In some embodiments, the shapes can encode or other correspond in a known, preselected manner to one or more identifying indicia for the detection assembly 10 such as a user identification code (e.g., player number other unique player identifier) or location of the impact pattern 32 on the user's body (e.g., specific location on the head). For example, various combinations dots, letters, numbers, and/or any other predetermined indicia corresponding to the encoded information can be included in the contact region 46 shape such that inspection of the pattern 32 allows the viewer to discern the encoded information. Different impact levels can be differentiable according to the shape and/or size of contact region 46/impact pattern 32, which can selected to be distinct for a given relief element 48 and which can be calibrated to establish a relative ordering of which regions 46/patterns 32 correspond to relatively higher or lower impact levels. Alternatively or additionally, different impact levels can differentiable according to the number of similarly shaped and sized regions 46/patterns 32 after a given impact (e.g., an impact generates a series of dots or lines resulting from a series of contact regions 46 having different separation distances, for example, where the number of dots or lines is proportional to the impact level).

Figure 6:
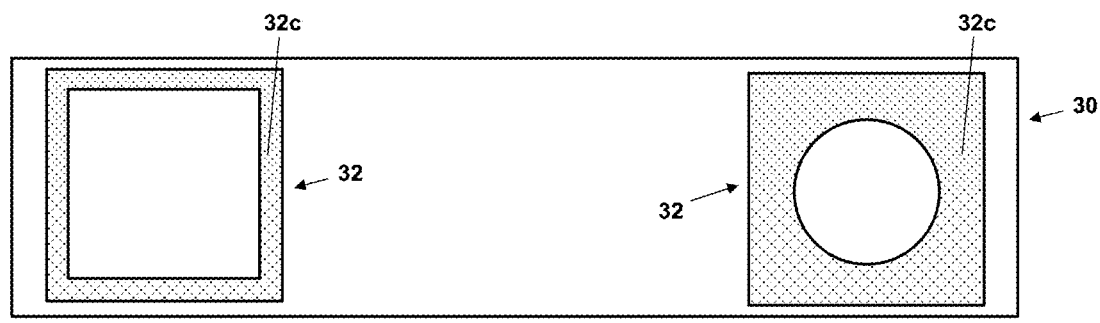
FIG. 6 is a bottom plan view B-B' of the multiple impact level detection assembly of FIG. 1 illustrating impact patterns after a low-level impact.
Figure 7:
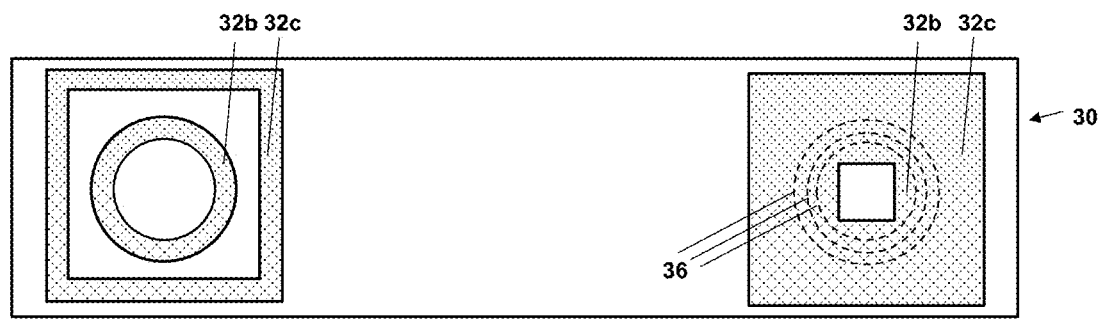
FIG. 7 is a bottom plan view B-B' of the multiple impact level detection assembly of FIG. 1 illustrating impact patterns after a medium-level impact.
Figure 8:
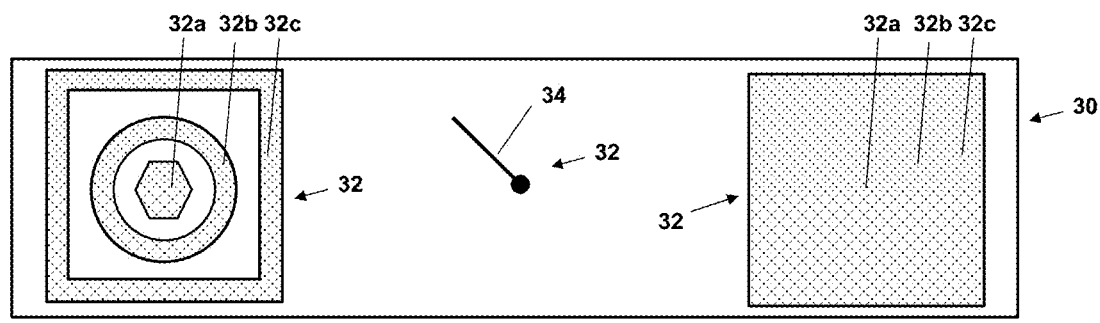
FIG. 8 is a bottom plan view B-B' of the multiple impact level detection assembly of FIG. 1 illustrating impact and torque patterns after a high-level impact.
Figure 9:
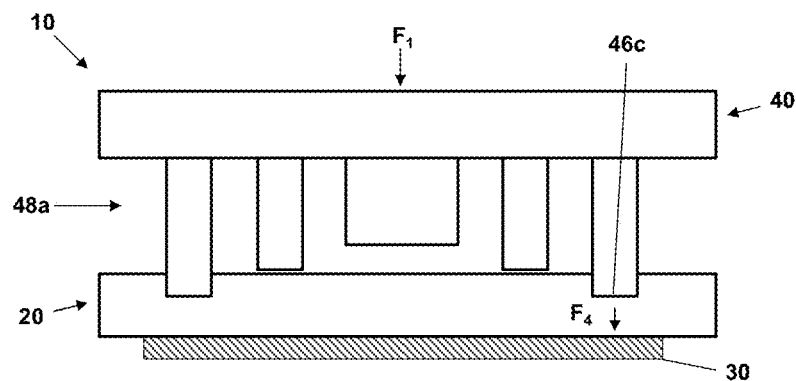
FIG. 9 is an expanded side cross sectional view of the multiple impact level detection assembly of FIG. 1 after a low-level impact.
Figure 10:
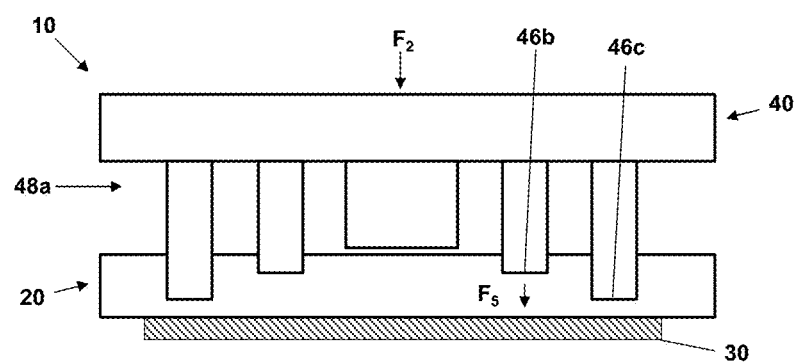
FIG. 10 is an expanded side cross sectional view of the multiple impact level detection assembly of FIG. 1 after a medium-level impact.
Figure 11:
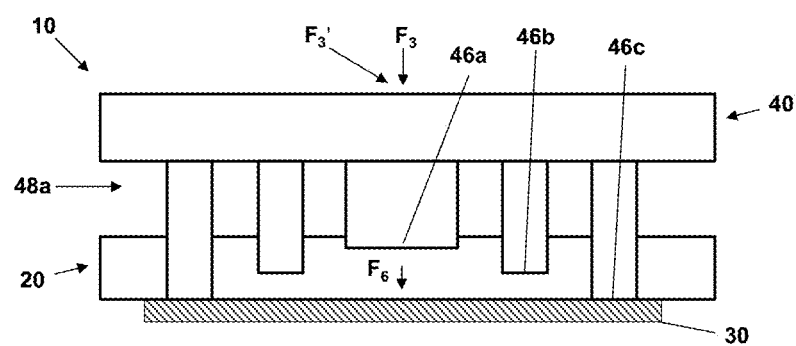
FIG. 11 is an expanded side cross sectional view of the multiple impact level detection assembly of FIG. 1 after a high-level impact.

FIGS. 6-11 illustrate the detection assembly 10 and resulting impact patterns 32 on the impact medium 30/first substrate 20 for a low-level impact (FIGS. 6 and 9), a medium-level impact (FIGS. 7 and 10), and a high-level impact (FIGS. 8 and 11). "Low," "medium," and "high" are relative terms and need not be associated with any particular impact or compression force, resulting pressure, and/or resulting torque. While different levels can be associated with a particular quantitative impact level if desired (e.g., as a result of calibration testing for the detection assembly), a relative qualitative comparison of values can be used to indicate whether a user (i.e., wearer) of the detection assembly 10 (e.g., alone or a part of a protective or other garment) has received a potentially dangerous impact (e.g., compressive and/or torqueing impact), or whether the user requires further investigation from a medical professional to determine whether the impact was dangerous or harmful.

Relative to FIG. 2 (which illustrates the detection assembly 10 in its natural, uncompressed state), the detection assembly 10 in FIGS. 6 and 9 has received a low-level impact with a compression force $F_1$ (FIG. 9). The compression force $F_1$ is illustrated as pushing on the relief substrate 40 top surface 42, although, depending on the orientation of the detection assembly 10 relative to impact (e.g., as worn by a user or incorporated into a garment), the compression force $F_1$ can be pushing on the first substrate 20 bottom surface 24 or on both substrates 20, 40. The compression force $F_1$ is high enough to force the furthest extending contact surfaces 46c of the relief element 48a sufficiently far into the first substrate 20 (e.g., by compressing, deforming, and/or penetrating a sufficiently soft or compliant first substrate 20 material) to apply a corresponding force $F_4$ to the impact medium 30 in the region of the contact surfaces 46c, which force $F_4$ exceeds the characteristic impact threshold for the detection medium 30. The compression force $F_1$ and the corresponding force $F_4$ do not necessarily apply the same pressure P to the impact medium 30 insofar as the relief substrate 40 top surface 42 (i.e., where $F_1$ is applied) and the contact surfaces 46c (where $F_4$ is applied) do not generally have the same cross sectional area A over which the force is applied (i.e., where P=F/A). As a result, the detectable property of the impact detection medium 30 is irreversibly generated on the detection medium 30 in the shape of an impact pattern 32. This result is illustrated in FIG. 6, with specific impact patterns 32c resulting from the contact surfaces 46c from the relief elements 48a and 48c. In this illustrative case, the compression force $F_1$ is insufficient for the relief element 48b to generate a corresponding impact pattern 32. Further, when the compression force is less than $F_1$, then no substantial impact pattern 32 is generated on the medium 30, even if the compression force is sufficient to compress the substrates 20, 40 together at least somewhat, because the corresponding force applied to the impact medium 30 in the region of the contact surfaces 46a does not exceed the characteristic impact threshold for the detection medium 30.

Relative to FIG. 2 and analogous to FIGS. 6 and 9, the detection assembly 10 in FIGS. 7 and 10 has received a medium-level impact with a compression force $F_2$ (FIG. 10), which is greater than the compression force $F_1$. As above, the compression force $F_2$ can be pushing on the relief substrate 40 top surface 42, on the first substrate 20 bottom surface 24, or on both substrates 20, 40. The compression force $F_2$ is high enough to force the middle and furthest extending contact surfaces 46b, 46c of the relief element 48a sufficiently far into the first substrate 20 to apply a corresponding force $F_5$ to the impact medium 30 in the region of the contact surfaces 46b, 46c, which force $F_5$ exceeds the characteristic impact threshold for the detection medium 30. As a result, the detectable property of the impact detection medium 30 is irreversibly generated on the detection medium 30 in the shape of an impact pattern 32. This result is illustrated in FIG. 7, with specific composite impact patterns 32b, 32c resulting from the contact surfaces 46b, 46c from the relief elements 48a and 48c. In this illustrative case, the compression force $F_2$ is still insufficient for the relief element 48b to generate a corresponding impact pattern 32.

FIG. 7 further illustrates an embodiment in which the impact detection medium 30 can incorporate one or more impact graduation indicia 36, which are representatively shown as concentric circles printed on the detection medium 30. The location of the impact graduation indicia 36 corresponds to the location of a sloped, non-parallel contact region 46 (e.g., the region 46b of the relief element 48c as shown). Because of the sloped surface of the contact region 46, the size and shape of the impact pattern 32b for the region 46b is proportional to the compression force received, and the impact graduation indicia 36 can be used to estimate the compression force received from within upper and lower bounds (e.g., as a result of calibration testing).

Relative to FIG. 2 and analogous to FIGS. 6 and 9, the detection assembly 10 in FIGS. 8 and 11 has received a high-level impact with a compression force $F_3$ (FIG. 11), which is greater than the compression force $F_2$. As above, the compression force $F_3$ can be pushing on the relief substrate 40 top surface 42, on the first substrate 20 bottom surface 24, or on both substrates 20, 40. The compression force $F_3$ is high enough to force the lowest, middle, and furthest extending contact surfaces 46a, 46b, 46c of the relief element 48 sufficiently far into the first substrate 20 to apply a corresponding force $F_6$ to the impact medium 30 in the region of the contact surfaces 46a, 46b, 46c, which force $F_6$ exceeds the characteristic impact threshold for the detection medium 30. As a result, the detectable property of the impact detection medium 30 is irreversibly generated on the detection medium 30 in the shape of an impact pattern 32. This result is illustrated in FIG. 8, with specific composite impact patterns 32a, 32b, 32c resulting from the contact surfaces 46b, 46c from the relief elements 48a and 48c. In this illustrative case, the compression force $F_3$ is sufficient for the relief element 48b to generate a corresponding impact pattern 32. When the compression force $F_3$ is substantially normal to the substrate 40 (and/or substrate 20), the impact pattern 32 can be in the form of a dot corresponding the point apex of the relief elements 48b. Alternatively, when a compression force $F_3'$ has both sufficient normal and shearing components relative to the substrate 40 (and/or substrate 20), a torqueing motion can result between the substrates 20, 40, and a resulting torque pattern 34 can provide an indication of both the magnitude and direction of the torqueing motion. Such an indication can provide information to a medical professional whether a user/wearer of the detection assembly has received a potentially dangerous torqueing impact, which can sometimes be more harmful than a purely compressive impact with the same intensity.

FIGS. 6-8 illustrate impact patterns 32 resulting from a uniform impact across the detection assembly 10. In some cases, a non-uniform impact on the detection assembly 10 can result in impact patterns 32 with different relative intensities in different locations. For example, with reference to FIGS. 6-8, a detection assembly 10 which receives a light impact on its left side but a heavy impact on its middle and right side (as viewed from plane B-B' in FIGS. 6-8) could exhibit the impact patterns 32 from the left side of FIG. 6 (i.e., impact pattern 32c on the left) and from the middle and right side of FIG. 8 (i.e., torque pattern 34 in the middle and composite impact patterns 32a, 32b, and 32c on the right). Such a spatial variability of the impact patterns can indicate where a user (i.e., wearer) of the detection assembly 10 has received a potentially dangerous impact (e.g., based on relative impact intensity as described above).

Figure 12:
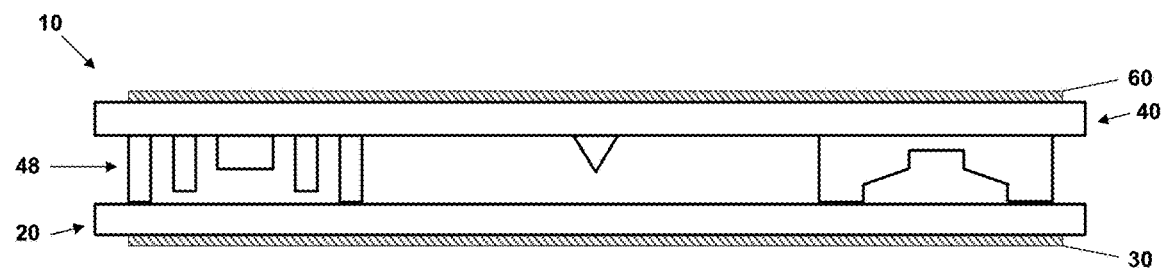
FIG. 12 is a side cross sectional view of the multiple impact level detection assembly of FIG. 1 further including an adhesive layer.

As illustrated in FIG. 12, the detection assembly 10 can include a means for attachment 60 on one or more of its external surfaces, thereby providing a means to fix the detection assembly 10 in place in a protective garment (or other garment article) and/or on a user's body. For example, the attachment means 60 can be used to attach the detection assembly 10 to a pad or shell component of a protective garment. In various embodiments, the attachment means 60 can be positioned on one or both of an outer surface of the first substrate 20 (e.g., on the top 22 or bottom surface 24 thereof) and an outer surface of the relief substrate 40 (e.g., on the top 42 or bottom surface 44 thereof), such as on the bottom surface 44 as illustrated in FIG. 12. The attachment means 60 is not particularly limited and can include any conventional means for fixedly or removably mounting/attaching two surfaces, such as an adhesive coating (e.g., pressure-sensitive adhesive, cured/dried glue composition) or a mechanical fastener (e.g., snaps, buttons, hook-and-loop fasteners, rivets, screws, etc.). The detection assembly 10 can include different types of attachment means 60, for example when more than one outer exposed surface includes the means 60.

In some embodiments, the detection assembly 10 or a component thereof (e.g., the first substrate 20, the relief substrate 40, and/or the impact detection medium 30) can be waterproof or water-resistant. This can be desirable when the detection assembly 10 during use is in close proximity to a user's body that is prone to moisture accumulation (e.g., via sweating by the wearer), for example adjacent to or in contact with the user's skin and/or hair (e.g., on the head). Excess moisture can damage the detection assembly 10 (e.g., causing the various components to become separated, detached, etc.). Waterproofing or water-resistance can be imparted to the detection assembly 10 or the component thereof by any suitable method known in the art, for example using a waterproof or water-resistant coating or film over the desired components (e.g., a silicone coating or film, a wax or paraffin coating of film, a non-water soluble polymeric coating or film such as polyethylene, preferably transparent when the coating or film covers the detection medium 30).

Figure 13:
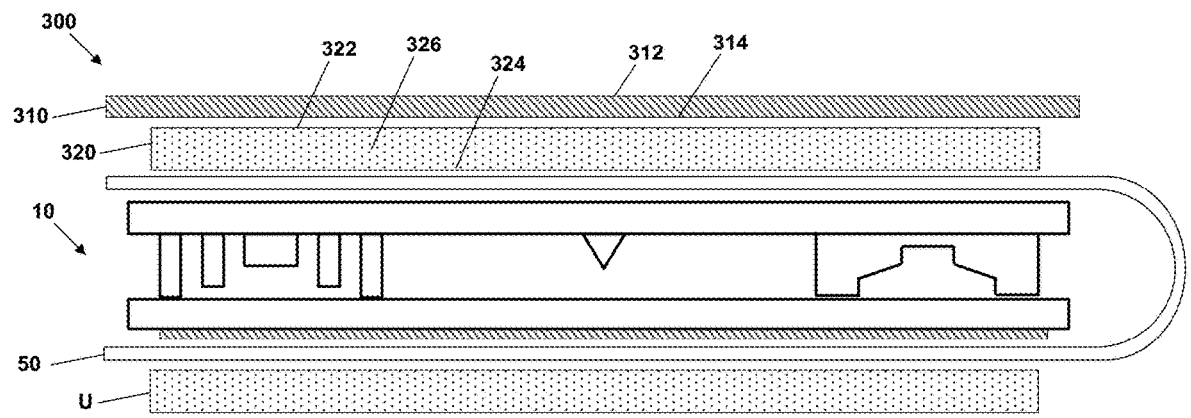
FIG. 13 is a side cross sectional view of the multiple impact level detection assembly of FIG. 1 further including a protective sleeve and as incorporated into a protective garment.

As illustrated in FIG. 13, the detection assembly 10 can include a sleeve 50 that at least partially (or completely) encloses the first substrate 20, the relief substrate 40, and the impact detection medium 30. The sleeve 60 can be waterproof or water-resistant as described above to prevent water damage to the assembly 10 components in the sleeve 50, such as from perspiration by a wearer of the assembly 10. The sleeve can include a waterproof or water-resistant coating or film as above, or it can be itself formed from a waterproof or water-resistant material (e.g., polymer or plastic material such as polypropylene). As shown in FIG. 13, the sleeve 50 can be partially open (e.g., open at one end and sealed at the sides and other end), thus allowing the detection assembly 10 or components thereof to slide easily into and out of the sleeve 50, while still providing substantial protection to the internal detection assembly 10 components. Suitably, the sleeve 50 can be an optically transparent or translucent material, thus providing optical access to internal detection assembly 10 components and permitting visual interrogation of the same after an impact. In other embodiments, the sleeve can be opaque.

In some embodiments, the first substrate 20 is adapted to be removable and replaceable. In such cases, the impact detection medium 30 suitably is positioned at one or more of the first substrate 20 top surface 22, the first substrate 22 interior volume 23, and the first substrate 22 bottom surface 24. This can represent a situation in which the first substrate 20 is a disposable, replaceable recording medium (i.e., because it includes the impact detection medium 30), and the relief substrate 40 can be a permanent fixture of the detection assembly 10 and/or a protective garment into which the detection assembly is incorporated. The first substrate 20 is suitably maintained in position relative to the relief substrate 40 in the detection assembly 10 via some non-fixed or non-permanent means. For example, the sleeve 50 assembly can hold the relief substrate 40 and the first substrate 20 in the same relative position during use. Once an impact has been received and recorded on the first substrate 20 impact detection medium 30, the first substrate 20 can be removed from the sleeve 50, and a new, non-impacted first substrate 20 can be inserted into the sleeve 50 for subsequent impact detection using the same (original) relief substrate 40. Other removable fastening means such as clamps or hook-and-loop fasteners (not shown) can be used to similarly hold the relief substrate 40 and the first substrate 20 in the same relative position during use while allowing simple removal and replacement of the first substrate 20 as desired.

In some embodiments, the detection assembly 10 can be configured to be worn on a person's head, whether alone or as incorporated into a protective garment or other garment. For example, the detection assembly 10 can be sized and shaped to partially or completely cover one or more cranial regions of a user's head, such as frontal or forehead region, side or temporal region, top or parietal region, and/or back or occipital region of the head. Alternatively or additionally, the detection assembly 10 can be configured to cover one or more a circumferential portion of the head (e.g., a headband shape alone or as part of an assembly covering a larger portion of the head), a lateral portion of the head (e.g., one or more side-to-side assembly structures), and a longitudinal portion of the head (e.g., one or more front-to-back assembly structures). For example, the detection assembly 10 can include elastic headwear configured to maintain the assembly 10 in a substantially fixed position on the wearer's head when worn. The elastic headwear can be a skull cap or a headband with one or more elastic portions. The first substrate 20 and/or the relief substrate 40 can be mounted to the headwear, for example with an adhesive or other attachment means 60 as described above, or by being located in a pouch in the headwear. Alternatively or additionally, the first substrate 20 and relief substrate 40 can be held in place on the wearer's head by the elastic force of the headwear when worn.

In some embodiments, the relief substrate 40 can include a plurality of relief elements 40 (e.g., as illustrated in FIG. 1). Each relief element 48 suitably includes at least two contact regions 46 having different separation distances H from the first substrate 20 top surface 22 (e.g., providing the multi-level impact sensitivity for the detection substrate 10). Individual relief elements 48 can have a surface area of about 1 cm$^2$ (e.g., a projected surface area on the relief substrate 40 bottom surface 44), for example at least about 0.1 cm$^2$, 0.2 cm$^2$, or 0.5 cm$^2$ and/or up to about 1.5 cm$^2$, 2 cm$^2$, 5 cm$^2$, or 10 cm$^2$. Additionally, individual relief elements 48 can be separated from neighboring relief elements 48 by distances of at least 0.2 cm, 0.5 cm, or 1 cm and/or up to 2 cm, 5 cm, or 10 cm to represent distinct measurement/interrogation areas of a user's body (e.g., head or otherwise) for the detection assembly. In some cases, the relief elements 48 can have a uniform size and shape on the relief substrate 40. Alternatively, the relief elements 48 have a variable size and/or shape on the relief substrate 40 (e.g., to provide further levels of impact sensitivity and/or impact level differentiation).

Figure 14:
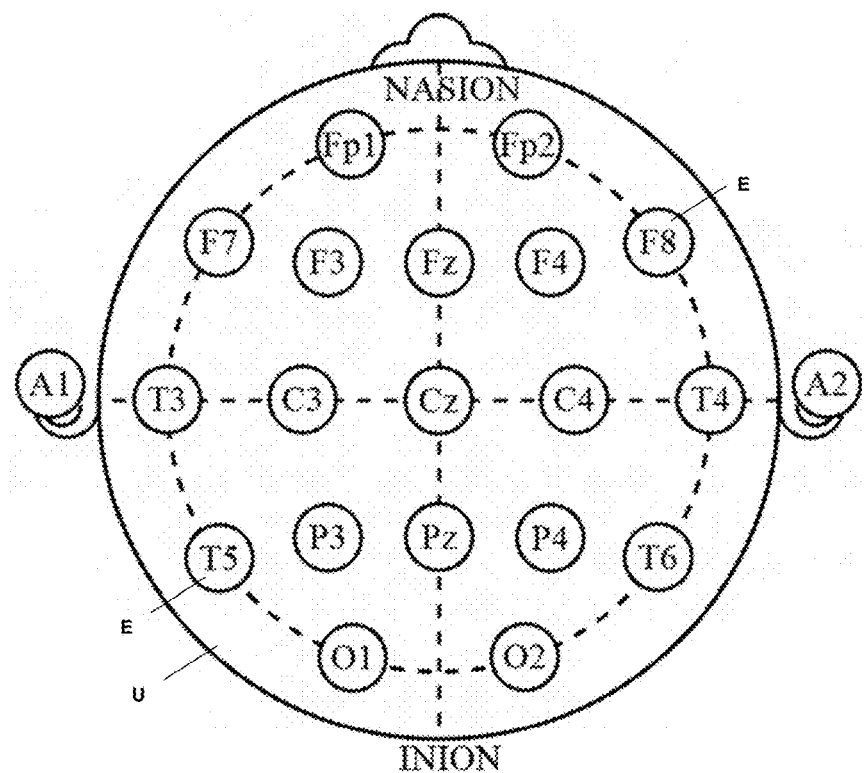
FIG. 14 is an electroencephalography (EEG) map illustrating standard interrogation points on a user's head according to the international 10-20 EEG system.
Figure 15:
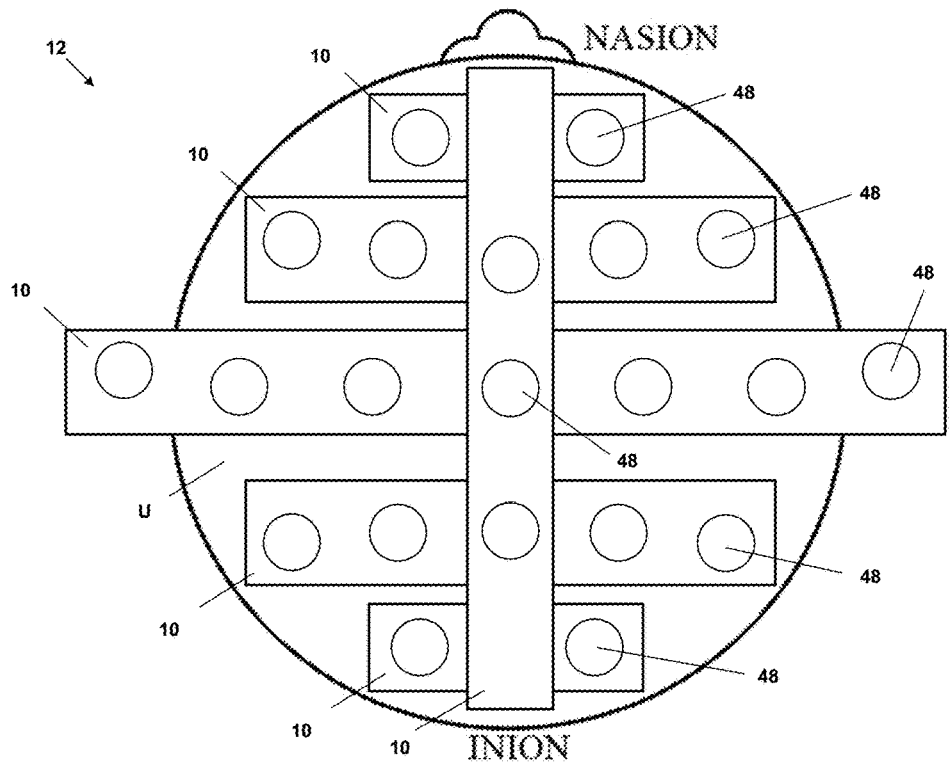
FIG. 15 is top plan view of a multiple impact level detection array according to the disclosure and including relief substrates at EEG locations of a user's head.

In some embodiments, the detection assembly 10 includes a plurality of relief elements 48 (e.g., with contact regions 46) and is configured to be worn on a person's head. For example, the relief elements 48 can be an array 12 of detection assemblies 10 such as in a mesh to be worn on a user's head, either alone or as part of a protective garment (e.g., as illustrated in FIG. 15). In a further refinement, the relief elements 48 can be positioned in locations corresponding to electroencephalography (EEG) locations on the wearer's head (e.g., at least 5, 8, 10, 12, or 15 EEG locations and/or up to 10, 15, 20, 25, 30, or 40 EEG locations). The EEG locations can be specified by any standard protocol, for example the international 10-20 system, which is an internationally recognized method to describe and apply the location of scalp electrodes in the context of an EEG test or experiment. As applied to the detection assembly 10 or array 12, the locations of the relief elements 48 and contact regions 46 can be selected to correspond to the EEG locations when the detection assembly 10 or array 12 is worn on the user's head. As understood by the skilled artisan, the "10" and "20" reflect that the distances between adjacent relief elements 48 are either 10% or 20% of the total front-back or right-left distance of the skull. FIG. 14 illustrates the EEG locations E on a human head of a user U. The letters F, T, C, P and O stand for frontal, temporal, central, parietal, and occipital lobes, respectively, and the EEG locations are determined relative to the nasion (i.e., the depressed area between the eyes, just above the bridge of the nose) and the inion (i.e., the lowest point of the skull from the back of the head and normally indicated by a prominent bump). FIG. 15 illustrates an array 12 of detection assemblies 10, where the relief elements 48 are positioned at EEG locations E. The detection assemblies 10 can include further relief elements 48 at additional, different locations (not shown), for example to provide impact detection information on smaller length scales than those provided by the EEG locations E.

FIGS. 16-20 illustrate particular embodiments of the first substrate 20 when it includes a plurality of microcapsules as a component of the impact detection medium 30.

Figure 16:
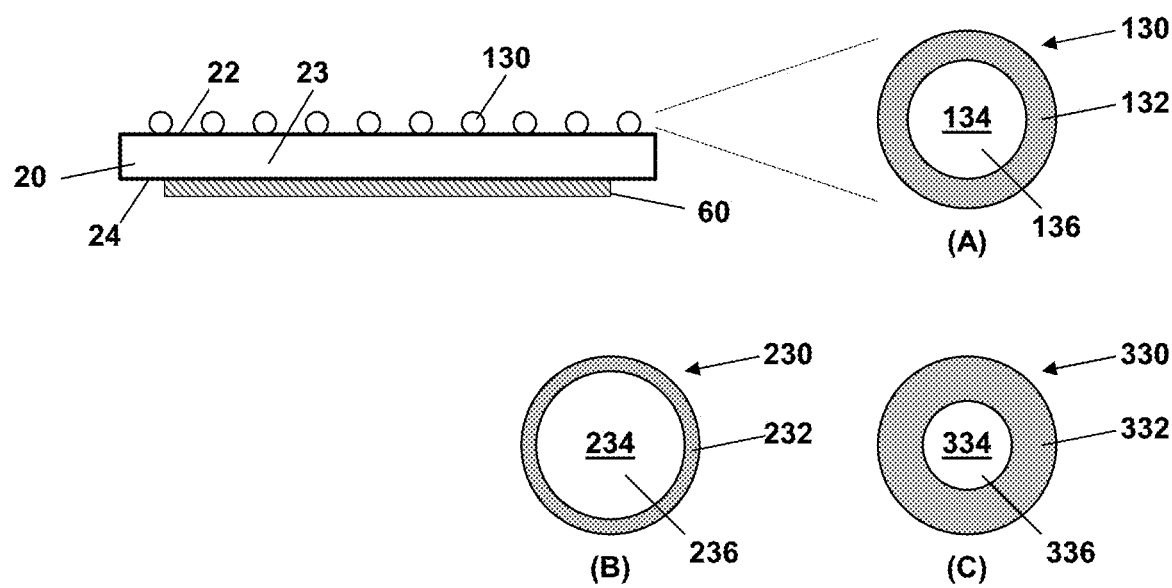
FIG. 16 is a side cross sectional view of an impact-detection substrate according to the disclosure and incorporating microcapsules on an exterior surface of the substrate, where insets A, B, and C illustrate different microcapsule structures.
Figure 17:
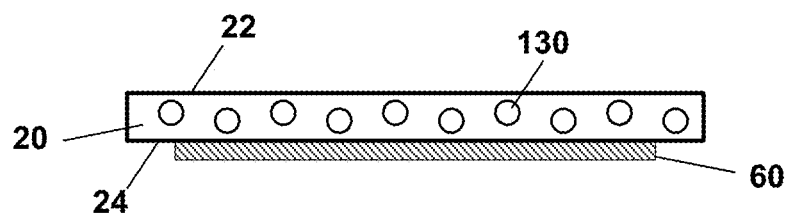
FIG. 17 is a side cross sectional view of an impact-detection substrate according to an additional aspect of the disclosure and incorporating microcapsules within the interior substrate volume.

With specific reference to FIGS. 16 and 17, the first substrate 20, having the top surface 22, the opposing bottom surface 24, and the interior substrate volume 23 includes a plurality of microcapsules 130 as the detection medium 30 which are positioned at one or more of the first substrate 20 top surface 22, the interior substrate volume 23, and the first substrate 20 bottom surface 24. In other embodiments, the microcapsules 130 additionally or alternatively can be located on the contact surfaces 46. Each microcapsule 130 has a characteristic impact threshold (e.g., based in its physical, mechanical, and chemical properties, as described below) which corresponds to a threshold impact event (e.g., compression and/or shear) above which the irreversible, detectable change associated with the microcapsule 130 and detection assembly 10 takes place. As illustrated in FIG. 16, the microcapsules 130 are positioned at the first substrate 20 top surface 22 (e.g., immobilized on the top surface 22 with an adhesive, a binder, or otherwise). FIG. 17 illustrates an embodiment in which the microcapsules 130 are positioned within the interior substrate volume 23 of first substrate 20 (e.g., distributed throughout the first substrate 20 as a composite material). The first substrate 20 further can include an attachment means 60 (as described above) disposed on any or several of its outer exposed surfaces, for example on the bottom surface 24 of the first substrate 20 as illustrated.

As illustrated in inset A of FIG. 1, a microcapsule 130 includes an outer shell 132 which defines (or encloses) an interior volume 134 of the microcapsule 130. An indicator 136 associated with the irreversible detectable change of the microcapsule 130 and detection assembly 10 is contained in the interior volume 134. The microcapsule 130 can be generally spherical in shape or otherwise, such as a cylindrical rod or disk, a prolate or oblate spheroid, etc. Suitable microcapsule 130 sizes are on the nanometer- or micrometer-scale, for example having a number-, volume-, or weight-based average, mean, median, or other characteristic size (e.g., diameter) in a range of about 10 nm to about 10 µm (e.g., at least 10 nm, 20 nm, 50 nm, 100 nm, or 200 nm and/or up to 100 nm, 200 nm, 500 nm, 1 µm, 2 µm, 5 µm, or 10 µm). The interior volume 134 is suitably sealed/closed relative to the external environment by the microcapsule 130 outer shell 132. In some embodiments, the outer shell 132 is suitably a polymeric shell material (e.g., an electrically conductive polymer or an electrically non-conductive polymer), such as polypyrrole, poly(methyl methacrylate), poly (benzyl methacylate), poly(lactic acid), poly(acrylic acid), polyaniline, or otherwise. In other embodiments, the microcapsule 130 is formed from a gellable hydrophilic colloid encapsulating material such as gelatin, gum arabic, agar, and combinations thereof. The indicator 136 is suitably contained within a fluid medium (e.g., water medium, water-containing medium, organic solvent medium such as a hydrophobic solvent or hydrophilic solvent, and mixtures thereof) inside the interior volume 134. The indicator 136 is suitably a colorant such as a non-toxic colorant. The indicator 136 can be dissolved, dispersed, emulsified, or otherwise mixed in the fluid medium. The fluid medium is suitably a non-toxic and/or a non-volatile carrier which can liquid and/or gel components.

The microcapsule 130 can be formed by any suitable method known in the art, for example including emulsion polymerization from an emulsion containing a fluid medium with the indicator 136 therein and a monomer corresponding to an outer shell 132 polymer. As the monomer is polymerized, it forms the shell 132 containing the indicator 136 therein. Kijewska et al. (2012), incorporated herein by reference, describes a suitable method of microcapsule 130 formation, which includes the photo-initiated emulsion polymerization of pyrrole monomer to form polypyrrole microcapsules 130 of relatively uniform size and containing any of a variety of materials (e.g., dyes, magnetic nanoparticles, ionic species) from the polymerization medium. Green et al. U.S. Pat. No. 2,730,457, incorporated herein by reference, describes a pressure-sensitive record material including rupturable microcapsules 130 of a film-forming hydrophilic colloid material (e.g., gelatin, gum arabic, agar, and combinations thereof) which contains a nucleus of liquid which is (or includes) at least one of two or more indicator 136 reactants which produce a distinctive color upon contact. Such reactants can include (colorless) phthalide dyes such as crystal violet lactone and/or malachite green lactone, and an oxidizing colorless compound such as benzoyl leuco methylene blue, which react with acidic substances to form the distinctive color. A suitable acidic substance includes acidic clays. The film-forming microcapsule 130 material and the acidic clay can be coated on a substrate such as paper; once a sufficient impact is received on the coated substrate, the microcapsules 130 rupture, releasing the colorless indicator 136, which then reacts with the acidic clay to form a visible color mark on the substrate corresponding to the location of the impact on the substrate. The coated substrate including the microcapsule 130 material and the acidic clay can be provided in the form of a tape material (e.g., further including an adhesive or other attachment means), and the coated substrate accordingly can be attached to the first substrate 20 to serve as the impact detection medium 30. Other suitable methods of microcapsule formation are described in Tiarks et al. (2001), Kamata et al. (2003), and Wang et al. (2008), all of which are incorporated herein by reference.

In an illustrative embodiment, the indicator 136 can include a hydrophobic colorant such as an oil-based paint or pigment in a hydrophobic liquid medium. Examples of suitable hydrophobic liquid media include oils such as vegetable oils (e.g., canola oil). The indicator 136 is a water-immiscible mixture which is then added to an aqueous reaction medium, which can include one or more water-miscible organic solvents (e.g., an alcohol-water mixture such as ethanol-water). The indicator 136 is then mixed or otherwise agitated with the aqueous reaction medium to form an emulsion of indicator 136 droplets in the reaction medium. The specific size (or size distribution) of indicator 136 droplets in the reaction medium can be selected or controlled, for example, by varying one or more of the degree of agitation or mixing, the selection and relative weight ratio of alcohol (or other water-miscible organic solvent) and water in the reaction medium, the weight ratio of reaction medium to the total indicator 136 added thereto, the selection of the hydrophobic liquid medium for the indicator 136, etc. Monomers for formation of a polymeric shell 132 are then added to the indicator 136 emulsion reaction medium along with any co-reactants, catalysts, and/or initiators desired for the polymerization. For example, pyrrole monomer and an aqueous iron (III) chloride oxidant solution can be added to the reaction medium. When polymerization is initiated the polymer (e.g., polypyrrole) forms as a shell 132 around the indicator emulsion 136 droplets, thereby forming a suspension of the microcapsules 130 in the reaction medium. The microcapsule 130 size and characteristic impact threshold can be controlled or selected, for example by varying one or more of the reaction/polymerization time, relative amount of monomer added to the reaction medium, and the emulsion droplet size. Once the polymerization reaction is complete, the microcapsules 130 can be collected/separated from the reaction medium by any suitable means (e.g., filtration) and incorporated into the first substrate 20 and the detection assembly 10 as generally described herein.

Each microcapsule 130 has a characteristic impact threshold prior to rupture of the microcapsule 130 and release of the indicator 136 from the interior volume 134 to generate an irreversible change in the detectable property associated with the indicator 136. When the microcapsule 130 experiences an impact force below the threshold value (e.g., compression force or shear force), the shock is absorbed by the microcapsule 130 (e.g., possibly causing it deform (reversibly or irreversibly), but not rupture or otherwise break). When the microcapsule 130 experiences an impact force above the threshold value, the microcapsule 130 breaks, releasing the indicator 136 and causing the irreversible detectable impact event associated therewith. The characteristic impact threshold is generally a function of the mechanical properties of the microcapsule 130 and its contents. Factors affecting the impact threshold can include, for example, diameter (D) or other characteristic size of the microcapsule 130/outer shell 132, thickness (T) of the outer shell 132 wall, mechanical/strength properties of the shell 132 material, and the material contained within the interior volume 134. Depending on the particular method used for making the microcapsule 130, the microcapsule material and corresponding geometric parameters of the microcapsule can be suitably controlled or selected to obtain a desired impact threshold. For example, when using an emulsion polymerization process (e.g., UV photo-initiated emulsion polymerization), the characteristic impact threshold of the microcapsule 130 can be been selected by controlling or selecting one or more polymerization reaction conditions, such as reaction solvent, polymerization initiator, monomer, ionic strength of reaction medium, reaction medium pH, reaction temperature, reaction time, emulsion droplet size, and UV light exposure.

A plurality of microcapsules 130 similarly has a characteristic impact threshold distribution associated therewith, which can result from capsule-to-capsule variability for individual microcapsules 130. Suitably, the variability is small and the corresponding impact threshold distribution is relatively narrow, thus reducing the likelihood or impact of false negatives or false positives resulting from individual microcapsules 130 which are stronger or weaker than intended. For example, on a number-, volume-, or weight-basis, the plurality of microcapsules 130 suitably has a characteristic impact threshold distribution such that at least 75%, 90%, 95%, or 99% of the microcapsules 130 have an individual characteristic impact threshold that is within 1%, 5%, 10%, or 25% of an average (or mean or median) impact threshold of the distribution. The desirably narrow impact threshold distribution can be obtained by forming the microcapsules 130 with correspondingly narrow distributions related to diameter and wall thickness.

In some embodiments, the detection assembly 10 and/or the first substrate 20 can incorporate a single plurality of microcapsules 130, all of which microcapsules 130 in the plurality are characterized by a single impact threshold distribution (e.g., all microcapsules 130 may be represented by a single distribution as represented above). In other embodiments, the detection assembly 10 can incorporate multiple different groups of microcapsules 130. For example, as illustrated in insets B and C of FIG. 16, a first microcapsule 230 includes an outer shell 232 which defines (or encloses) an interior volume 234 of the first microcapsule 230, and a second microcapsule 330 includes an outer shell 332 which defines (or encloses) an interior volume 334 of the second microcapsule 330. As qualitatively illustrated, the outer shell 232 is thinner than the outer shell 332, and the characteristic impact threshold of the first microcapsule 230 can be correspondingly smaller than that of the second microcapsule 330 (e.g., when the diameter and other properties of the two microcapsules 230, 330 are the same or substantially similar). Thus, in some embodiments, the detection assembly 10 can include a plurality of the first microcapsules 230 having a first characteristic impact threshold and a plurality of the second microcapsules 330 having a second characteristic impact threshold (e.g., where the first characteristic impact threshold is different from the second characteristic impact threshold). Suitably, the detectable property of the first indicator 236 is different from the detectable property of the second indicator 336.

The first and second detectable properties can be different, for example, by using different indicators or by using the same indicators at different concentrations or in other ways to provide different responses. As noted above, different impact thresholds are controllable or selectable by varying wall thickness, microcapsule diameter, polymerization conditions, polymer selection, etc. In this way, microcapsules with different impact threshold levels and different detectable properties (e.g., different generated colors) allow for differentiation of low/high impacts. This can provide a means for impact-level differentiation in addition to the incorporation of relief substrates 40 with variable-height contact surfaces 46 as described above. For example, the first characteristic impact threshold may be 100 units (e.g., arbitrary relative units corresponding to impact force), and the second characteristic impact threshold may be 200 units, where the threshold levels are selected to correspond to warning and damage levels, for instance. When the detection assembly 10 is incorporated into a personal protective garment or other garment worn by a user, a detection corresponding to the low threshold may indicate the possibility of a damaging impact to the user (e.g., and the user may need medical attention), and a detection corresponding to the high threshold may positively indicate a damaging impact to the user (e.g., and the user should receive immediate medical attention). Although described in the context of two distinct types of microcapsules 230, 330, detection assembly 10 according to the disclosure more generally can include any number of different microcapsule types (e.g., n different microcapsule types with n different detectable properties and/or n different impact thresholds, such as n being at least 2, 3, or 5 and/or up to 3, 5, 10, or 20).

Figure 18:
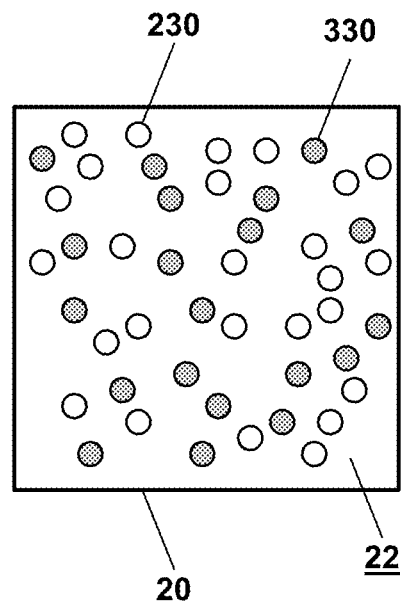
FIG. 18 is a top view of an impact-detection substrate according to an additional aspect of the disclosure and incorporating a plurality of different microcapsule types homogeneously distributed throughout a substrate surface.
Figure 19:
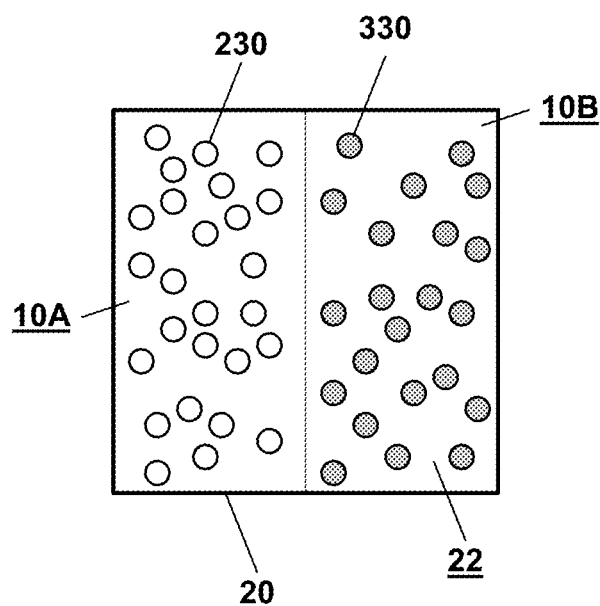
FIG. 19 is a top view of an impact-detection substrate according to an additional aspect of the disclosure and incorporating a plurality of different microcapsule types spatially segregated in different regions of a substrate surface.
Figure 20:
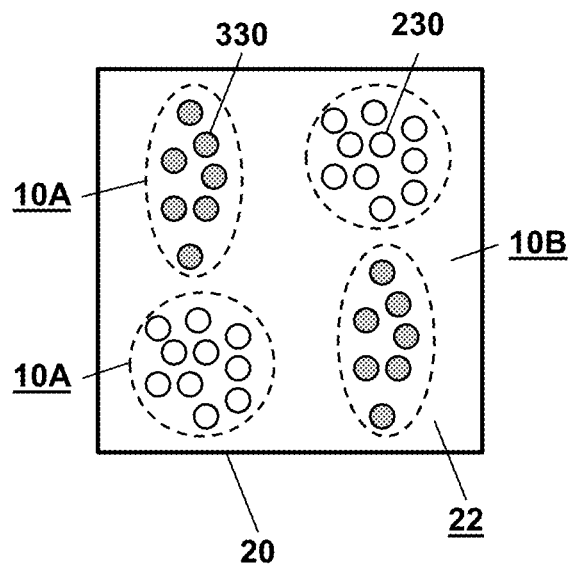
FIG. 20 is a top view of an impact-detection substrate according to an additional aspect of the disclosure and incorporating a plurality of different microcapsule types spatially segregated in different regions of a substrate surface.

FIGS. 18-20 illustrate some first substrate 20 embodiments incorporating the different microcapsules 230, 330.

In FIG. 18, the plurality of the first microcapsules 230 and the plurality of the second microcapsules 330 are homogeneously distributed throughout a region of the first substrate 20. The combination of high- and low-impact detection microparticles mixed together provides spatially integrated result over the substrate 20 area. A low impact releases just the first indicator 236, and a high impact releases both the first and second indicators 236, 336. Detection of neither indicator in an area means that the area sustained no impact above the low threshold; detection of just the first indicator 236 in an area means that the area sustained an impact between the low and high thresholds; and detection of at least the second indicator 336 (or both indicators 236,336) in an area means that the area sustained an impact above the high threshold. As an illustrative example, a yellow optical indicator may be used for the first indicator 236 and a blue optical indicator may be used for the second indicator 336. In such case, a detectable yellow result means an impact was between the low and high impact threshold levels, while a detectable green result (e.g., indicative of blue and yellow mixing) means impact was above the high impact threshold levels. Thus, the detection assembly 10 provides an irreversible spatial contour impact map (which can be integrated over substrate area) showing areas of (i) below low impact, (ii) between high and low impact and (iii) above high impact. In an extension, more contours/impact levels are possible using more distinct indicators having differentiable detectable properties when cumulatively ruptured.

In FIG. 19, the plurality of the first microcapsules 230 and the plurality of the second microcapsules 330 are spatially segregated in separate regions 10A, 10B of the first substrate 20. Such separation into distinct regions 10A, 10B can be used to differentiate different impact levels among them, for example where the different regions 10A, 10B represent more and less impact-sensitive regions of an article incorporating the detection assembly 10 (e.g., a human body part protected by a protective garment incorporating the detection assembly 10). In this embodiment, it is also possible for the first and second detectable properties to be the same (e.g., same colors) or different, because a known, preselected spatial segregation of the microcapsules 230, 330 can differentiate the high/low impact results even if the detectable properties are the same.

FIG. 20 illustrates an embodiment in which the microcapsules 230, 330 are spatially positioned on the substrate 20 to define one or more areas 10A containing the microcapsules 230, 330 and one or more areas 10B free (or substantially free) from microcapsules 230, 330. Although FIG. 20 illustrates two types of microcapsules 230, 330, different refinements can include only one or more than two types of microcapsules. In another refinement, the areas 10A can be padding protection areas having a shape corresponding to protective padding for a protective garment (e.g., which facilitates the incorporation of the detection assembly 10 into an existing protective garment, such as when the detection assembly 10 includes a suitable means for attachment 60 for installation). A padding protection area can be a single unitary area in the shape of a protective pad (e.g., the shape of the outer or inner surface thereof, depending on the intended padding surface for attachment), and/or it can be a plurality of areas which collectively are in the shape of a protective pad (e.g., when the padding consists of multiple separate pieces for mounting within a protective garment). In a helmet setting as detailed below, the padding areas can correspond to sections for the back of the head, the sides of the head, the forehead, and/or the dome of the head.

The detectable property associated with the indicator 136 can be a property of the indicator 136 itself and/or a property of the environment surrounding the microcapsule 130 and affected by the indicator 136 after rupture of the microcapsule 130 and release of the indicator 136. The detectable property can variously correspond to an irreversible transition from a first state to a second state for the microcapsule 130 and/or indicator 136 in which the property is (i) detectable in the first state but not the second state, (ii) detectable in the second state but not the first state, or (iii) detectable but different in both states. Detection can be by human inspection (e.g., visual inspection or smelling for optical or olfactory indicators, respectively) or machine-assisted for the particular property being detected. The detectable property can include one or more of an optical property, an olfactory property, a chemical property, an electrical property, and an electromagnetic property associated with the indicator 136.

An optical property can correspond to color change or color generation, electromagnetic radiation emission at one or more wavelengths (e.g., light in the UV, visible, and or IR spectrum), or optical transmission at one or more wavelengths (e.g., in the UV, visible, and or IR spectrum). As noted, optical properties can be detectable by visual inspection (human eye), by conventional optical detection equipment, or both. Example optical indicators include dyes or pigments having a detectable color in the visible spectrum and fluorophores excitable with incident light and producing a detectable UV or visible light emission. Suitable fluorescent probes and indicator dyes (e.g., pH-sensitive, $Ca^{2+}$-sensitive, or otherwise) include fluoresceins, carboxyfluoresceins, hydroxypyrenes, rhodamines, disodium fluorescein, nile red, nile blue, cresyl violet, and acridine orange (e.g., available from Sigma-Aldrich, St. Louis, Mo.). Example calcium indicators (molecular probes) include calcium green, calcium orange, calcium crimson, fluoresceins, furanosines, indocyanines, and rhodamines (e.g., life technologies products available from Thermo Fisher Scientific, Waltham, Mass.). Such dyes, pigments, and/or fluorophores can be dissolved or suspended in a fluid medium contained within the microcapsule 130 prior to rupture and released therefrom after rupture. In some embodiments, the optical indicator can initially be undetectable (e.g., clear or colorless) when inside the microcapsule 130, becoming optically detectable only after rupture and release from the microcapsule 130. For example, the underlying substrate 20 can include an indicator-activating agent (e.g., an acid or base for pH-sensitive indicators or a $Ca^{2+}$-containing substance for $Ca^{2+}$-sensitive indicators), which causes the optical indicator to become optically detectable after release and contact with the activating agent. Alternatively or additionally, other microcapsules containing the indicator-activating agent and having the same or similar rupture characteristics as those containing the optical indicator can be included on the substrate 20 and intermingled with the microcapsules 130 (e.g., where initially segregated indicator and activating agent in different microcapsules combine after rupture to become detectable). In other embodiments, the optical indicator can initially be in a detectable form when inside the microcapsule 130. In such cases, the optical indicator can be masked from detection prior to rupture and release from the microcapsule 130 based on the optical properties of the microcapsule 130 wall. For example, the microcapsule 130 can be formed from a light-absorbing polymer (e.g., poly (pyrrole) which absorbs light across the visible spectrum or other polymer which is suitably doped to absorb light); after microcapsule 130 rupture, the optical indicator is exposed to external (e.g., ambient) light and can be optically detected.

An olfactory property can correspond to the generation of a detectable scent (e.g., by human nose), such as resulting from the release of a scented olfactory indicator from the microcapsule 130 after rupture. Example olfactory indicators include any of a variety of inorganic or organic compounds at a concentration/amount sufficient to generate a detectable scent upon release, for instance linear, cyclic, and/or aromatic organic compounds having one or more aldehyde, ketone, and/or alcohol functional groups such as biacetyl, camphor, or cinnamaldehyde.

A chemical property can correspond to the generation of a detectable chemical property, which itself could be detectable, for example including the release of an acid or base indicator detectable as pH value after rupture. Similarly, the microcapsule 130 rupture event could induce a different detectable chemical property, for example pH change resulting from the release of an acid or base indicator which then induces a color change via a pH indicator external to the ruptured microcapsule 130, for example a pH indicator incorporated on or in the substrate 20 (or 40) surrounding the microcapsule 130.

An electrical property can correspond to the generation of a voltage or current, a change in conductivity, etc. following release of an electrical indicator. Example electrical indicators include (aqueous) solutions with one or more metal-containing compounds such as metal salts (e.g., alkali or alkali earth metal salt with an organic or inorganic anion such as a halogen). For instance, the detection substrate 20 can include wires or other electrical leads that do not form a complete electrically conductive path between electrical input and output regions of the substrate when initially formed. When the electrical indicator is (for example) an aqueous metal salt solution (e.g., sodium chloride) contained in the microcapsule 130, rupture of the microcapsule 130 can release the metal salt, which in turn provides detectable electrical connectivity between the previously unconnected electrical leads.

EXAMPLES

The following examples illustrate the disclosed articles and methods, but are not intended to limit the scope of any claims thereto.

Example 1

Example 1 illustrates the incorporation of a multiple impact level detection assembly 10 spatially positioned into/onto a protective garment to detect shock experienced by a wearer of the protective garment. In some embodiments, the protective garment is a helmet (e.g., sporting helmet such as for football, hockey, biking, skiing, motorcycling, snowmobiling, racing, etc.; combat helmet, construction or safety helmet). In other embodiments, the protective garment is a wearable guard for other than a head body part (e.g., chest, shoulder, back, arm, groin, leg, etc. for sporting in general or a specific sport such as those above).

Figure 21:
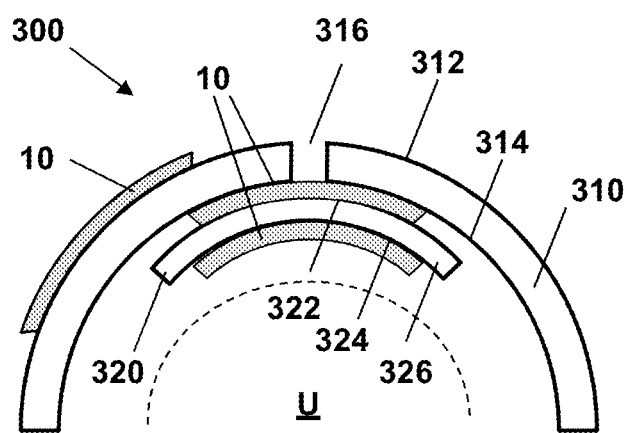
FIG. 21 is a side cross sectional view of a protective garment incorporating an impact-detection substrate according to the disclosure.

FIG. 21 illustrates a protective garment 300 according to the disclosure. The protective garment 300 in FIG. 21 is illustrated in a generally curved shape suitable for a helmet, but it can correspond to other garment types as noted above. The protective garment 300 includes a protective shell 310 having an outer surface 312 and an opposing inner surface 314. The protective shell 310 is generally a rigid, impact-resistant material such as formed from a plastic/polymeric material or composite (e.g., molded polycarbonate for football helmets). For the protective shell 310, the outer surface 312 is a relative term denoting the external surface exposed to the environment and/or representing the impact surface when the protective garment 300 is worn by a user or wearer U, and the inner surface 314 similarly represents the surface internal to the protective garment 300 and closest to the user U when worn. The protective garment 300 further includes protective padding 320 having an outer surface 322, an opposing inner surface 324, and an interior padding volume 326 between the outer surface 322 and the inner surface 324. The protective padding 320 is mounted at the outer surface 322 thereof to the protective shell 310 at the inner surface 314 thereof (e.g., directly or indirectly with a detection assembly 10 or other intervening component). The protective padding 320 is generally a soft, flexible impact-absorbing material such as formed from polymeric foams, gels, cloth/fabric, inflatable gas (air) bladders, etc. (e.g., example: poly(vinyl nitrile) foam, expanded polypropylene foam of varying densities encased in a shell such as polyethylene for football helmets). Similar to the protective shell 310, the protective padding 320 outer surface 322 is a relative term denoting the surface closest to the protective shell 310 and farthest away from the user U when the protective garment 300, and the inner surface 324 represents the surface internal to the protective garment 300 and closest to the user U when worn. Two surfaces/structures mounted to each other (e.g., the protective shell 310 and the protective padding 320) can be fixedly or removably attached to each other (e.g., generally in a fixed position relative to each other while mounted), either directly or indirectly, such as by any suitable means for attachment. Example means for attachment can include those described above for the detection assembly 10, including adhesive coatings, mechanical fasteners, etc.

As further shown in FIG. 21, the detection assembly 10 can be incorporated into the protective garment 300 at any of a variety of locations. For example, the detection assembly 10 can be positioned at one or more of an interface between the protective shell 310 inner surface 314 and the protective padding 320 outer surface 322, the interior padding volume 326, the protective padding 320 inner surface 324, and the protective shell 310 outer surface 312. The detection assembly 10 can be mounted or adhered to the protective shell 310 and/or protective padding 320 using the means for attachment described above, for example an attachment means 60 incorporated as a component of the detection assembly 10 and/or as part of the shell 310 or padding 320. In a refinement, the detection assembly 10 is mounted to the padding 320 inner surface 324, and the detection assembly 10 can be viewed for impact patterns 32 by simply removing the protective garment 300 and inspecting the garment 300 interior, in particular when the impact detection medium 30 and corresponding impact patterns 32 are positioned at a viewable surface of the detection assembly 10 (e.g., on the first substrate 20 bottom surface 24 as illustrated in FIG. 13). In another refinement, the protective shell 310 can include a viewport 316 (e.g., an open area or a transparent window or section of the shell 310) configured to provide optical access from the protective shell 310 outer surface 312 to the interface between the protective shell 310 inner surface 314 and the protective padding 320 outer surface 322. Positioning of a detection assembly 10 at this interface provides a convenient manner for optical detection (visual or otherwise) of an optically detectable property associated with the indicator 36 of the detection assembly 10

(e.g., line-of-sight inspection of the detection assembly 10 without having to remove the garment 300 from the user U).

Example 2

Example 2 illustrates the use of microencapsulated stock (MES) as disclosed in U.S. Pat. No. 2,730,457 in the form of impact tape. MES has only two conditions: colorless (inactivated) and colored (activated). This renders MES incapable of measuring pressure in a calibrated sense. MES functions as a digital record (yes/no) but not as a graduated sensor indicating that a pressure of some force per unit area has been applied. Creating such a calibrated sensor using MES as the recording media in a detection assembly according to the disclosure is illustrated in this example. Pressure is equal to force divided by area. By using a specially textured relief surface, the digital yes/no result of the MES is converted into a graduated pressure (and, accordingly, force) sensor. The acceleration experienced in an impact also can be determined if the mass of the object exerting the force is known. Accordingly, the disclosed detection assembly may be considered an inexpensive accelerometer containing no electronics and providing a permanent record of multiple level of impact received by the detection assembly.

Pressure/force calibration will depend on the MES, the pattern chosen, and the actual application. When used in a helmet, it will depend on the mass of the head, and the specific helmet pad. Calibration depends on the helmet design, padding and expected weight of the head. Therefore it is possible to provide sufficient calibration to ensure impact levels are recorded such that non-medical experts can easily determine if a particular impact is acceptable, intense, or a cause for concern, for example. The detection assembly serves as a graduated pressure meter based on the MES paper and a calibrated relief pattern that bestows the MES paper with calibrated pressure sensing properties.

Figure 22:
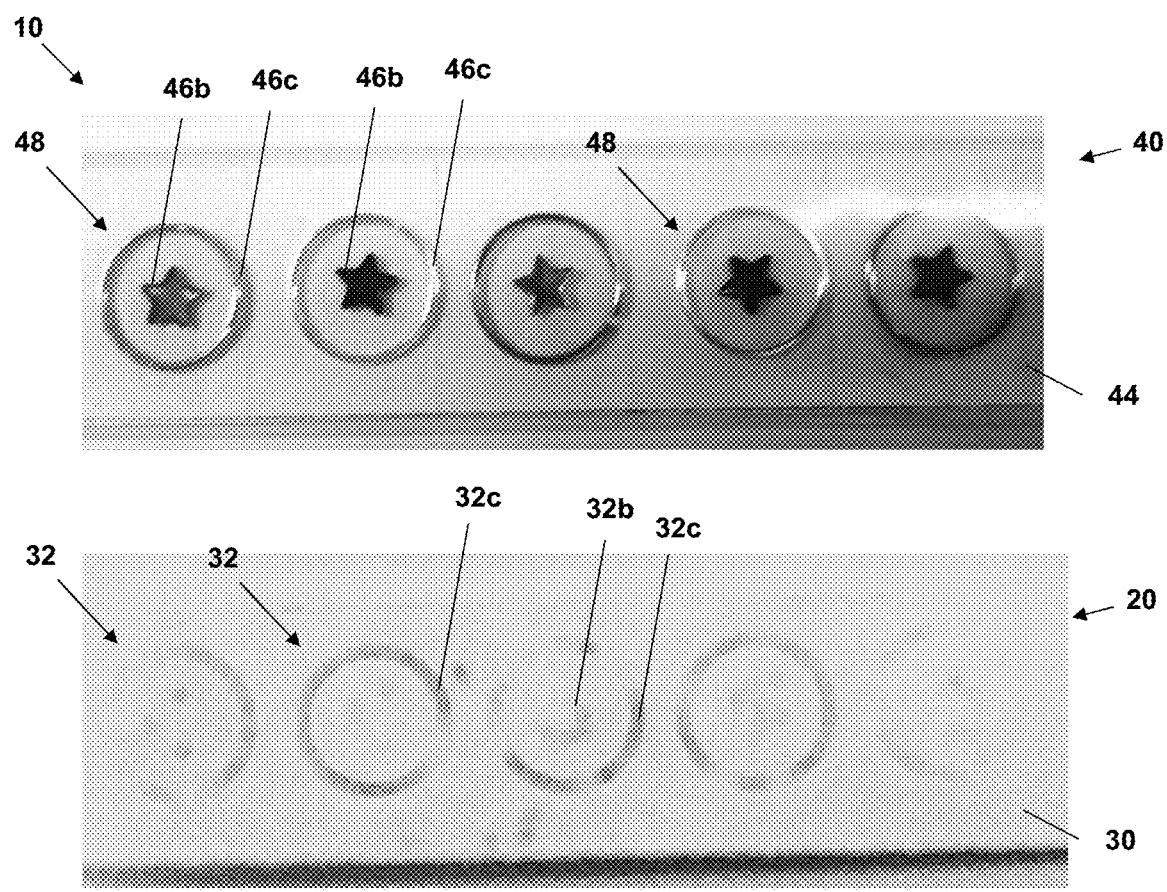
FIG. 22 illustrates a detection assembly according to the disclosure including a relief substrate with relief elements (top panel) and a microencapsulated stock impact detection medium on a first substrate (bottom panel).

FIG. 22 illustrates a detection assembly 10 according to the disclosure using the MES as an impact detection medium 30. The MES 30 in the form of impact tape was adhered to a flexible piece of cardstock serving as the first substrate 20. A relief substrate 40 was similarly formed from cardstock, and relief elements 48 were affixed to a bottom surface 44 of the relief substrate 40. As illustrated, the relief elements 48 included a circular metallic ring as a contact region 46c and a star-shaped metallic element as a contact region 46b. The circular metallic ring had larger height than the star-shaped metallic element. The relief substrate 40 and the first substrate 20 were then fixed in a face-to-face orientation (e.g., as illustrated in FIG. 3, right side) with a clear plastic sleeve (not shown) to form the detection assembly 10. In this state, the circular metallic ring contact region 46c was in contact with the impact medium 30 and had a zero separation distance therefrom. Similarly, the star-shaped metallic element contact region 46b was spaced apart from the impact medium 30. The detection assembly 10 was then subjected to a test impact. As shown, the strongest impact was recorded by the middle relief elements 48, which had correspondingly darker impact patterns 32c and included an impact pattern 32b representing the highest impact force. Milder impacts were recorded at the peripheral relief elements 48, were a faint outline of the outer impact pattern 32c was noted. This illustrates that the detection assembly 10 provides a calibrated impact detection response that also is spatially dependent based on the location of the impact.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the articles, compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

While various embodiments have been disclosed herein, other modifications may be made that are within the scope of the articles, apparatus, and methods of the present disclosure. For example, alternate force recording substrates, relief patterns, sensor positions, means to fasten the sensors on sports equipment and sleeves to facilitate changing the disposable recording tapes can be employed consistent with the described function. The disclosed embodiments are exemplary in nature and variations that do not depart from the spirit of the disclosure are intended to be within the scope of the same. Such variations are not to be regarded as a departure from the spirit and scope of the disclosure.

PARTS SUMMARY

10: multiple impact level detection assembly
12: multiple impact level detection array
20: first substrate
22, 24, 23: top surface, bottom surface, and interior volume of first substrate
30, 130, 230, 330: impact detection medium (e.g., microcapsules)
32, 32a, 32b, 32c: impact patterns
34: torque pattern
36: impact graduation indicia
132, 232, 332: outer shell
134, 234, 334: interior volume
136, 236, 336: indicator
40: relief substrate
42, 44, 43: top surface, bottom surface, and interior volume of relief substrate
46, 46a, 46b, 46c: contact region of relief substrate bottom surface (parallel and sloped surfaces for impact detection, sharp edges and points for torque detection)
48, 48a, 48b, 48c: relief elements
50: sleeve
60: means for attachment (e.g., adhesive)
300: protective garment for user U
310: protective shell
312, 314: outer surface, inner surface of protective shell
320: protective padding 322, 324, 326: outer surface, inner surface, and interior volume of protective padding
E: EEG locations on a user's head
H: separation distance
N: surface normal vector
U: user/wearer of protective garment (e.g., head)
W: characteristic lateral length scale (e.g., diameter or width) of relief element

REFERENCES

1. Kijewska et al., Chem. Eur. J., 18:310-320 (2012)
2. Tiarks et al., Langmuir, 17:908-918 (2001)
3. Kamata et al., J. Am. Chem. Soc., 125:2384-2385 (2003)
4. Wang et al., Chem. Mater., 20:848-858 (2008)
5. Green et al. U.S. Pat. No. 2,730,457 (1956)
6. Lee et al. U. S. Pat. No. 5,142,309 (1992)

What is claimed is:

1. A multiple impact level detection assembly comprising:
   (a) a first substrate having a top surface, an opposing bottom surface, and an interior substrate volume between the top surface and the bottom surface;
   (b) a relief substrate having a top surface, an opposing bottom surface, and an interior substrate volume between the top surface and the bottom surface, wherein:
      (i) the relief substrate bottom surface opposes the first substrate top surface, and
      (ii) the relief substrate bottom surface comprises at least two contact regions having different separation distances from the first substrate top surface, wherein the at least two contact regions are capable of contacting the first substrate under compression; and
   (c) an impact detection medium positioned at the first substrate interior volume, wherein the impact detection medium has a characteristic impact threshold for generating a detectable property associated with the impact detection medium.

2. The multiple impact level detection assembly of claim 1, further comprising an additional impact detection medium positioned at the first substrate top surface.

3. The multiple impact level detection assembly of claim 1, further comprising an additional impact detection medium positioned at the first substrate bottom surface.

4. The multiple impact level detection assembly of claim 1, further comprising an additional impact detection medium positioned at the relief substrate contact regions.

5. The multiple impact level detection assembly of claim 1, wherein the contact regions have a general shape selected from the group consisting of a flat surface parallel to the opposing first substrate top surface, a curved or flat surface sloped relative to the opposing first substrate top surface, an edge, a point, and combinations thereof.

6. The multiple impact level detection assembly of claim 1, wherein the assembly is configured to be worn on a person's head.

7. The multiple impact level detection assembly of claim 6, further comprising elastic headwear configured to maintain the assembly in a substantially fixed position on the person's head when being worn.

8. The multiple impact level detection assembly of claim 1, wherein the relief substrate comprises a plurality of relief elements, each relief element comprising at least two contact regions having different separation distances from the first substrate top surface.

9. The multiple impact level detection assembly of claim 8, wherein the relief elements have a uniform size and shape on the relief substrate.

10. The multiple impact level detection assembly of claim 8, wherein the relief elements have a variable size and shape on the relief substrate.

11. The multiple impact level detection assembly of claim 8, wherein:
    (i) the assembly is configured to be worn on a person's head, and
    (ii) the relief elements are positioned in locations corresponding to electroencephalography (EEG) locations on the person's head when worn.

12. The multiple impact level detection assembly of claim 1, wherein the separation distance for at least one contact region is zero.

13. The multiple impact level detection assembly of claim 1, further comprising:
    (d) a sleeve at least partially enclosing the first substrate, the relief substrate, and the impact detection medium.

14. The multiple impact level detection assembly of claim 1, wherein:
    the first substrate is adapted to be removable and replaceable.

15. The multiple impact level detection assembly of claim 1, wherein at least one of the first substrate and the relief substrate are optically translucent or transparent.

16. The multiple impact level detection assembly of claim 1, further comprising a means for attachment on one or both of an outer surface of the first substrate and an outer surface of the relief substrate.

17. The multiple impact level detection assembly of claim 1, wherein the detectable property is an optical property.

18. The multiple impact level detection assembly of claim 1, wherein the impact detection medium comprises a plurality of microcapsules each comprising an outer shell defining an interior volume and an indicator contained in the interior volume, wherein each microcapsule has a characteristic impact threshold prior to rupture of the microcapsule and release of the indicator from the interior volume to generate an irreversible change in a detectable property associated with the indicator.

19. The multiple impact level detection assembly of claim 18, wherein the detectable property is selected from the group consisting of an optical property, an olfactory property, a chemical property, an electrical property, an electromagnetic property, and combinations thereof.

20. The multiple impact level detection assembly of claim 18, wherein the plurality of microcapsules comprises:
    (A) a plurality of first microcapsules containing a first indicator therein and having a first characteristic impact threshold; and
    (B) a plurality of second microcapsules containing a second indicator therein and having a second characteristic impact threshold;
    wherein:
        the detectable property of the first indicator is different from the detectable property of the second indicator, and
        the first characteristic impact threshold is different from the second characteristic impact threshold.

21. An article of clothing comprising the multiple impact level detection assembly of claim 1 spatially positioned in or on the article of clothing to detect impact experienced by a wearer of the article of clothing.

22. A protective garment comprising the multiple impact level detection assembly of claim 1 spatially positioned in or on the protective garment to detect impact experienced by a wearer of the protective garment.

23. A protective garment comprising:
    (a) a protective shell having (i) an outer surface and (ii) an opposing inner surface;
    (b) protective padding having (i) an outer surface, (ii) an opposing inner surface, and (iii) an interior padding volume between the outer surface and the inner surface, wherein the protective padding is mounted at the outer surface thereof to the protective shell at the inner surface thereof; and
    (c) the multiple impact level detection assembly of claim 1 positioned at one or more of: (i) an interface between the protective shell inner surface and the protective padding outer surface, (ii) the interior padding volume, (iii) the protective padding inner surface, and (iv) the protective shell outer surface.

24. The protective garment of claim 23, wherein the protective garment is a helmet.

25. The protective garment of claim 23, wherein the protective garment is a wearable guard for other than a head body part.

26. The protective garment of claim 23, wherein the multiple impact level detection assembly is positioned at the interface between the protective shell inner surface and the protective padding outer surface.

27. The protective garment of claim 23, wherein the multiple impact level detection assembly is positioned at the protective padding inner surface.

28. The protective garment of claim 23, wherein the multiple impact level detection assembly is positioned such that the impact detection medium can be interrogated by visual inspection when the protective garment is not being worn and without disassembling the protective garment.

29. A method for equipping a protective garment with a means for detecting impact, the method comprising:
    (a) providing a protective garment comprising:
        (i) a protective shell having (A) an outer surface and (B) an opposing inner surface, and
        (ii) protective padding having (A) an outer surface, (B) an opposing inner surface, and (C) an interior padding volume between the outer surface and the inner surface;
    (b) attaching the multiple impact level detection assembly of claim 1 to one or more of:
        (i) the protective padding outer surface, and
        (ii) the protective padding inner surface; and
    (c) mounting the protective padding at the outer surface thereof to the protective shell at the inner surface thereof.

30. A kit comprising:
    (a) a multiple impact level detection assembly of claim 1; and
    (b) protective padding sized and shaped for insertion into a protective shell of a protective garment, the protective padding having (i) an outer surface, (ii) an opposing inner surface, and (iii) an interior padding volume between the outer surface and the inner surface.

31. A method for detecting impact on a protective garment worn by a user, the method comprising:
    (a) wearing the protective garment according to claim 23;
    (b) impacting the protective garment; and
    (c) interrogating the impact detection medium of the protective garment after (b) to determine whether the protective garment has sustained an impact force exceeding a characteristic impact threshold at one or more of the contact surfaces of the relief substrate.

32. The method of claim 31, wherein:
    the contact regions have a general shape selected from the group consisting of an edge, a point, and combinations thereof; and
    interrogating the impact detection medium comprises determining whether the protective garment has sustained a torqueing impact and the direction of same.

33. The method of claim 31, further comprising:
    (d) if the protective garment has sustained an impact force exceeding the characteristic impact threshold, determining whether the impact force is dangerous to the user.

34. A kit comprising:
    (a) a multiple impact level detection assembly of claim 1; and
    (b) an elastic wearable garment adapted to maintain the detection assembly in position relative to a user's body.

35. The kit of claim 34, wherein the garment is a headband.

36. The kit of claim 34, wherein the garment is a cap.

37. The kit of claim 34, wherein the kit comprises a plurality of the multiple impact level detection assemblies which are adapted to replace an existing multiple impact level detection assembly mounted in the garment.

38. The multiple impact level detection assembly of claim 1, wherein:
    the assembly further comprises an additional impact detection medium positioned at the first substrate bottom surface; and
    the assembly is configured to be worn on a person's head.

* * * * *